United States Patent
Schilling et al.

(10) Patent No.: US 10,307,599 B2
(45) Date of Patent: *Jun. 4, 2019

(54) MANAGING TELEMETRY COMMUNICATION MODES OF A DEVICE

(71) Applicant: Medtronic, Inc., Minneapolis, MN (US)

(72) Inventors: Eric A. Schilling, Ham Lake, MN (US); Christopher T. House, Pine Island, MN (US); Gary P. Kivi, Maple Grove, MN (US); Karen J. Kleckner, Blaine, MN (US); John W. Komp, Silverthorne, CO (US); Nicholas C. Wine, Minneapolis, MN (US); Matthew R. Yoder, Crystal, MN (US); Bo Zhang, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/918,033

(22) Filed: Mar. 12, 2018

(65) Prior Publication Data
US 2018/0200525 A1 Jul. 19, 2018

Related U.S. Application Data

(63) Continuation of application No. 15/141,421, filed on Apr. 28, 2016, now Pat. No. 9,913,989.

(51) Int. Cl.
*A61N 1/00* (2006.01)
*A61N 1/372* (2006.01)
(Continued)

(52) U.S. Cl.
CPC ........ *A61N 1/37223* (2013.01); *A61B 5/0031* (2013.01); *A61N 1/362* (2013.01);
(Continued)

(58) Field of Classification Search
CPC .......................... A61B 5/031; A61N 1/37223; A61N 1/37252; A61N 1/362; A61N 1/37217; H04L 2209/88
See application file for complete search history.

(56) References Cited

U.S. PATENT DOCUMENTS 6,564,104 B2 5/2003 Nelson et al.
7,110,823 B2 9/2006 Whitehurst et al.
(Continued)

OTHER PUBLICATIONS (PCT/US2017/025821) PCT Notification of Transmittal of the International Search Report and the Written Opinion of the International Searching Authority, dated Jul. 24, 2017, 10 pages.

*Primary Examiner* — Mallika D Fairchild

(57) ABSTRACT

Systems, apparatus, methods and computer-readable storage media facilitating management of operation of an implantable medical device ("IMD") using a number of communication modes are provided. An IMD is configured to operate in a disabled mode wherein radio frequency (RF) telemetry communication is disabled, or operate in a first advertising mode using the RF telemetry communication. The IMD receives a clinician session request from a clinician device via an induction telemetry protocol while operating in the disabled mode or the first advertising mode, and transitions to operating from the disabled mode or the first advertising mode to operating in a second advertising mode based on receiving the clinician session request. From the second advertising mode, the IMD can establish a clinician telemetry session with the clinician device using the RF telemetry communication and a unique security mechanism facilitated by an identifier for the clinician device included in the clinician session request.

21 Claims, 13 Drawing Sheets

(51) Int. Cl.
  *H04W 4/80* (2018.01)
  *A61B 5/00* (2006.01)
  *A61N 1/362* (2006.01)
  *H04W 12/08* (2009.01)
  *H04L 29/08* (2006.01)
  *H04W 52/02* (2009.01)
  *H04W 80/10* (2009.01)
  *G16H 40/63* (2018.01)
  *G16H 40/67* (2018.01)
  *H04L 29/06* (2006.01)

(52) U.S. Cl.
  CPC ..... *A61N 1/37217* (2013.01); *A61N 1/37252* (2013.01); *A61N 1/37276* (2013.01); *G16H 40/63* (2018.01); *G16H 40/67* (2018.01); *H04L 67/12* (2013.01); *H04L 67/125* (2013.01); *H04L 67/142* (2013.01); *H04W 4/80* (2018.02); *H04W 12/08* (2013.01); *H04W 52/028* (2013.01); *H04W 80/10* (2013.01); *H04L 63/0876* (2013.01); *H04L 63/101* (2013.01); *H04L 2209/88* (2013.01); *Y02A 90/26* (2018.01); *Y02D 70/00* (2018.01); *Y02D 70/10* (2018.01); *Y02D 70/14* (2018.01); *Y02D 70/142* (2018.01); *Y02D 70/144* (2018.01); *Y02D 70/162* (2018.01); *Y02D 70/166* (2018.01); *Y02D 70/26* (2018.01)

(56) References Cited

U.S. PATENT DOCUMENTS

| | | |
|---|---|---|
| 8,145,320 B2 | 3/2012 | Corndorf et al. |
| 8,386,051 B2 | 2/2013 | Rys |
| 8,475,372 B2 | 7/2013 | Schell et al. |
| 8,594,801 B2 | 11/2013 | Corndorf et al. |
| 9,072,914 B2 | 7/2015 | Greenhut et al. |
| 9,288,614 B1 | 3/2016 | Young et al. |
| 9,687,658 B2 | 6/2017 | Wu et al. |
| 9,855,433 B2 | 1/2018 | Shahandeh et al. |
| 9,894,691 B1 | 2/2018 | Hellman |
| 2010/0106224 A1 | 4/2010 | Von Arx et al. |
| 2011/0153420 A1 | 6/2011 | Harvey |
| 2011/0202113 A1 | 8/2011 | Persson et al. |
| 2012/0172690 A1 | 7/2012 | Anderson et al. |
| 2012/0220351 A1 | 8/2012 | Kerai et al. |
| 2014/0330327 A1 | 11/2014 | Thompson-Nauman et al. |
| 2015/0065047 A1 | 3/2015 | Wu et al. |
| 2015/0133951 A1 | 5/2015 | Seifert et al. |
| 2015/0148868 A1 | 5/2015 | Shahandeh et al. |
| 2015/0341785 A1 | 11/2015 | Young et al. |
| 2018/0021589 A1 | 1/2018 | Wu et al. |

MANAGING TELEMETRY COMMUNICATION MODES OF A DEVICE

This application is a continuation of U.S. patent application Ser. No. 15/141,421 (published as U.S. Patent Publication No. 2017/0312530) filed Apr. 28, 2016, issuing as U.S. Pat. No. 9,913,989, the entire content of which is incorporated herein by reference in its entirety.

TECHNICAL FIELD

This disclosure relates generally to implantable devices and, more particularly, to systems, apparatus, methods and computer-readable storage media facilitating telemetry communication mode management in an implantable device.

BACKGROUND

Implantable medical devices (IMDs) are often utilized in modern healthcare to facilitate the ability for patients to lead healthy and full lives. For example, IMDs such as pacemakers, implantable cardioverter-defibrillators (ICDs), neurostimulators, and drug pumps can facilitate management of a wide range of ailments, including, but not limited to, cardiac arrhythmias, diabetes, and Parkinson's disease. Patients and medical care providers can monitor the IMD and assess a patient's current and historical physiological state to identify conditions or predict impending events.

The sophistication of IMDs is evolving to provide for advanced computing and telemetry capabilities. One hurdle to achieving such highly functional devices is efficient power management. In particular, many implantable devices operate from power sources that have a limited lifespan and/or are not rechargeable. As such, after the implantable device is implanted within the human body and the lifespan of the power source has been reached, the implantable device may need to be removed. Another challenge associated with employing telemetry communication to wirelessly communicate information between an IMD and an external device concerns data security. Thus systems, apparatus, methods and computer-readable storage media that employ and/or manage different communication modes to facilitate data security while providing efficient power consumption are desired.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodiments beyond those described in the Summary section.

Embodiments described herein include systems, apparatus, methods and computer-readable storage media that facilitate management of telemetry communication modes of an implantable device. In some embodiments, the implantable device is or includes an IMD. In other embodiments, the implantable device is or includes a device configured to interact with the IMD. In these embodiments, both the implantable device and the IMD can be implanted within a patient.

In one embodiment, an IMD is provided. The IMD includes a housing configured to be implanted at least partially within a patient. The IMD also includes a memory, coupled to the housing, that stores executable components, and circuitry, coupled to the housing, and configured to at least one of obtain sensed physiological data associated with the patient or deliver a therapy to the patient. The IMD also includes a processor coupled to the housing that executes the executable components stored in the memory. The executable components include at least a communication component configured to facilitate telemetry communication between the implantable device and one or more external devices using a first telemetry communication protocol and a second telemetry communication protocol to communicate data associated with at least one of the sensed physiological data or the therapy, and a communication mode management component configured to control operation of the implantable device in different communication modes. The different communication modes include a disabled mode configured to prevent telemetry communication between the implantable device and the one or more external devices according to the first telemetry communication protocol and enable telemetry communication between the implantable device and the one or more external devices according to the second telemetry communication protocol. The communication modes also include a first advertising mode configured to facilitate establishment of a first type of telemetry communication session between the implantable device and the one or more external devices using the first telemetry communication protocol, and a second advertising mode configured to facilitate establishment of a second type of telemetry communication session between the implantable device and the one or more external devices using the first telemetry communication protocol.

In one implementation, the first type of telemetry communication session includes a monitoring telemetry session wherein the implantable device and the one or more external devices are authorized to communicate first data packets according to first communication parameters. The second type of telemetry communication session includes a clinician telemetry session wherein the implantable device and the one or more external devices are authorized to communicate the first data packets and second data packets according to second communication parameters less restrictive than the first communication parameters. In some embodiments, during the first advertising mode, the communication component can transmit one or more first advertisement data packets according to the first telemetry communication protocol at a first defined rate, and during the second advertising mode the communication component can transmit one or more second advertisement data packets according to the first telemetry communication protocol at a second defined rate faster than the first defined rate.

In various implementations, the communication mode management component can be configured to transition operation of the implantable device from the disabled mode or the first advertising mode to the second advertising mode based on reception, by the communication component, of a clinician session request according to the second telemetry communication protocol from a clinician device of the one or more external devices, wherein the clinician session request includes a request to establish a second type of telemetry communication session with the implantable device using the first telemetry communication protocol.

The clinician session request further includes an identifier for the clinician device that restricts establishment of the second type of telemetry communication session between the implantable device and the clinician device.

The different communication modes can further include a clinician mode wherein the communication component performs the second type of telemetry communication session between the implantable device and the clinician device using the first telemetry communication protocol, and wherein the communication mode management component can be configured to transition operation of the implantable device from the second advertising mode to the clinician mode in response to establishment of the second type of telemetry communication session between the implantable device and the clinician device based on the identifier for the clinician device included in the clinician session request. The different communication modes can further include a standby mode wherein the communication component performs the second type of telemetry communication session between the implantable device and the clinician device with a reduced functionality relative to a functionality employed during the clinician mode, resulting in reduced power consumption of a power source of the implantable device during the standby mode relative to a power consumption of the clinician mode.

Additional embodiments are directed to a method for managing operation of an implantable device using different communication modes. The method includes facilitating, by an implantable medical device including a processor, telemetry communication between the implantable medical device and one or more external devices using a radio frequency telemetry communication protocol and a non-radio frequency telemetry communication protocol, and controlling, by the implantable medical device, operation of the implantable medical device in different communication modes. The different communication modes include a first advertising mode configured to facilitate establishment of a first type of telemetry communication session between the implantable medical device and the one or more external devices using the radio frequency telemetry communication protocol, and a second advertising mode configured to facilitate establishment of a second type of telemetry communication session between the implantable medical device and a clinician device of the one or more external devices using the radio frequency telemetry communication protocol based on reception, by the implantable medical device, of a session initiation request from the clinician device via the non-radio frequency telemetry communication protocol.

In one or more implementations, the controlling includes transmitting, by the implantable medical device, one or more first advertisement data packets according to the radio frequency telemetry communication protocol at a first defined rate during the first advertising mode, and transmitting, by the implantable medical device, one or more second advertisement data packets according to the radio frequency telemetry communication protocol at a second defined rate faster than the first defined rate during the second advertising mode. The controlling can further include, operating, by the implantable medical device, in the disabled mode, or operating, by the implantable medical device, in the first advertising mode, and transitioning, by the implantable medical device, from the operating in the disabled mode or the operating in the first advertising mode to operating in the second advertising mode based on reception, by the implantable medical device, of a clinician session request according to the non-radio frequency telemetry communication protocol from a clinician device of the one or more external devices, wherein the clinician session request includes a request to establish a second type of telemetry communication session with the implantable medical device using the first telemetry communication protocol.

In another implementation, the method includes transitioning, by the implantable medical device, from the operating in the second advertising mode to the operating in the disabled mode based on failure of the implantable medical device and the clinician device to establish the second type of telemetry communication session within a defined time period, and a determination that usage of the first telemetry communication protocol by the implantable device is undesirable or unsafe based on a defined context of the implantable device. For example, the implantable device can determine that usage of the first telemetry communication protocol by the implantable device is undesirable or unsafe based on at least one of: no detection of implantation of the implantable medical device into a body, enablement of a magnetic imaging mode of the implantable medical device, or disablement of a remote monitoring functionality of the implantable medical device.

In one or more additional embodiments, a non-transitory computer readable medium is provided that includes computer executable instructions that, in response to execution, cause an implantable device including at least one processor to perform various operations. These operations include operating in a disabled mode, including preventing telemetry communication by the implantable device using a radio frequency telemetry protocol or operating in a first advertising mode, including transmitting first advertisement data packets according to the radio frequency telemetry protocol at a first rate. The operations further include receiving a clinician session initiation request from a clinician device via an induction telemetry protocol while operating in the disabled mode or the first advertising mode, the clinician session initiation request including an identifier for the clinician device, and transitioning to operating from the disabled mode or the first advertising mode to operating in a second advertising mode based on the receiving the clinician session initiation request, which includes transmitting second advertisement data packets according to the radio frequency telemetry protocol at a second rate.

In some implementations, the operations can further include: generating clinician session authorization information based on the receiving the clinician session initiation request, wherein the authorization information includes a unique session identifier and at least one unique session key; and employing the authorization information to facilitate establishment of a clinician telemetry session with the clinician device.

Still in other embodiments, a system is disclosed that includes a first external device configured to perform telemetry communication session with other devices, and an implantable device. The implantable device is configured to: operate in a first advertising mode that includes facilitating establishment of a first type of telemetry communication session between the implantable device and the first external device or a second external device using a first telemetry communication protocol; and operate in a second advertising mode that includes facilitating establishment of a second type of telemetry communication session between the implantable device and the first external device using the first telemetry communication protocol, wherein the implantable device is configured to operate in the second advertising mode based on reception of a clinician session initiation request from the first device via a second telemetry communication protocol.

In one or more implementations, the implantable device is further configured to: generate authorization information based on the reception of the clinician session initiation request, wherein the authorization information includes a unique session identifier and at least one unique session key; and employ the authorization information to establish the second type of telemetry communication session with the first external device. The implantable device is further configured to operate in the first advertising mode again based on closing of the second type of telemetry communication with the first external device, and cause the authorization information to be unusable to establish the second type of telemetry communication session with the first external device at a later time based on the closing of the second type of telemetry communication session.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification can be employed. Other advantages and novel features of the embodiments described will become apparent from the following detailed description of the specification when considered in conjunction with the drawings.

DETAILED DESCRIPTION OF DRAWINGS

Figure 1:
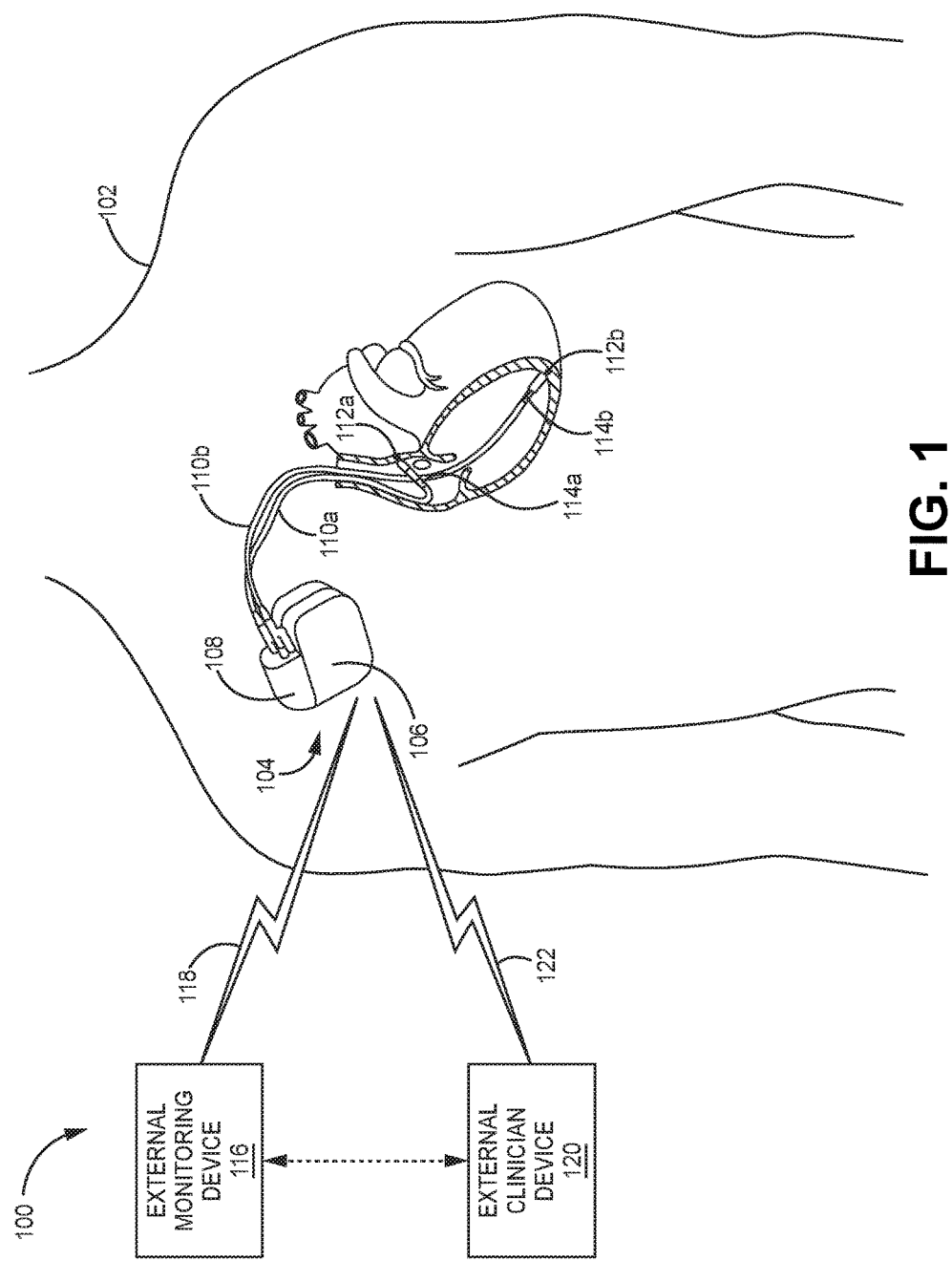
FIG. 1 illustrates a schematic diagram of an example, non-limiting medical device telemetry system configured to facilitate managing telemetry communication modes of an implantable device in accordance with one or more embodiments described herein.

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

The subject disclosure describes systems, apparatus, methods and computer-readable storage media that employ and/or manage different communication modes to facilitate data security while providing for efficient power consumption. In various embodiments, systems, apparatus, methods and computer-readable storage media are provided that facilitate enhanced battery conservation associated with telemetry operations of an implantable device by employing different communication modes of operation that are respectively associated with different amounts of battery drain The different amounts of battery draw associated with these different communication modes are attributed to activation of different types of telemetry hardware circuitry components of the implantable device (e.g., radio frequency (RF) components and induction components), and different amounts of activation of the respective telemetry hardware circuitry components (e.g., different duty cycles for receiver and transmitter activation). Because activation and deactivation of different telemetry hardware circuitry components involves physical and electrical processes and components, a human is unable to replicate or perform the subject battery conservation techniques. In addition, the subject battery conservation techniques provide substantial improvements in the field of implantable device telemetry operations while facilitating different types of telemetry communication by an implantable device. The disclosed systems, apparatus, methods and computer-readable storage media further provide substantial improvements in the field of implantable medical device telemetry security. In particular, the subject systems, apparatus, methods and computer-readable storage media facilitate enhanced security associated with establishing and performing a telemetry session with the implantable device using a RF-based telemetry communication technology/ protocol that enables rapid (and high power consuming) bi-directional telemetry communication with the implantable device of data considered highly invasive or sensitive (e.g., programming data or waveform data associated with a clinician session).

With reference now to the drawings, FIG. 1 illustrates a schematic diagram of an example, non-limiting medical device telemetry system 100 configured to facilitate managing telemetry communication modes of operation of an implantable device in accordance with one or more embodiments described herein. In the embodiment shown, medical device telemetry system 100 includes an implantable device 104 implanted within a body 102, an external monitoring device 116, and an external clinician device 120. In some embodiments, the implantable device 104 is an IMD that can also be configured to facilitate one or more diagnostic or treatment functions relative to the body 102 of a patient. In other embodiments, the implantable device 104 is separate from an IMD (not shown in this embodiment) that is also implanted within the body 102 and communicatively and/or electrically coupled to the IMD. Still in another embodiments, the implantable device 104 can include a medical device that can be implanted within the body or employed outside of the body to apply a medical drug or therapy to the body, such as an insulin pump.

Embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

One or more embodiments of medical device telemetry system 100 are described in connection with managing various telemetry communication modes of operation of the implantable device 104 in association with performing telemetry communication with one or more external devices, such as external monitoring device 116 and/or external clinician device 120. These external devices can include a variety of external device types, including, but not limited to, a tablet computer associated with a patient or a physician, a smartphone associated with a patient or a physician, a medical device associated with a patient or a physician, an electronic device at a home of a patient or at an office of a physician, an off-the-shelf device purchased at a store, etc.

The implantable device 104 can use wireless telemetry to exchange various types of information with external devices including external monitoring device 116 and external clinician device 120. For example, using wireless telemetry, the implantable device 104 can transmit information to the external monitoring device 116 and/or the external clinician device 120 including, but not limited to, sensed physiological or biometric data from the body 102, diagnostic determinations made based on the sensed physiological or biometric data, therapy data associated with a therapy delivered to the body, and/or performance data regarding operation and performance of the implantable device 104 (e.g., power level information, information regarding strengths of signals received, information regarding frequency of received interrogation requests, remaining battery life, etc.). In some implementations, the implantable device 104 is an IMD configured to sense the physiological data or the biometric data from the body 102. The IMD can also provide therapy to the body 102 and retain the therapy information regarding the therapy that was provided. In other implementations, the implantable device 104 is associated with an IMD configured to sense the physiological or biometric data or provide the therapy to the body 102.

In another example, the external monitoring device 116 and/or the external clinician device 120 can employ telemetry communication to read data captured by the implantable device 104. For instance, the external monitoring device 116 and/or the external clinician device 120 can read electrogram data captured by the implantable device 104 or other physiological or biometric data sensed by the implantable device 104. In another example, using wireless telemetry, the external monitoring device 116 can send information or signals to the implantable device 104 to program the implantable device 104 or to configure or re-configure the implantable device 104.

In various embodiments, the implantable device 104, the external monitoring device 116, and/or the external clinician device 120 can communicate using commercially available RF based communication protocols and technologies. By way of example, but not limitation, the communication protocols can include, but are not limited to, BLUETOOTH®, BLUETOOTH® low energy (BLE), near field communication (NFC), Wireless Fidelity (Wi-Fi) protocol, ZIGBEE®, RF4CE, WirelessHART, 6LoWPAN, Z-Wave, ANT, and the like. There is a desire to use commercially available telemetry communication protocols for wireless communication between implantable devices and external devices (e.g., implantable device 104 and external monitoring device 116 or external clinician device 120) in order to more easily facilitate widespread provisioning of telemetry solutions. For example, many modern mobile devices such as smartphones, tablet personal computer (PC), and the like are configured to communicate using various publically available telemetry protocols.

The implantable device 104, the external monitoring device 116 and/or the external clinician device 120 can communicate using commercially available and/or proprietary communication protocols and technologies that involve non-RF-based wireless communication technologies. For example, in one or more embodiments, the implantable device 104, the external monitoring device 116 and/or the external clinician device 120 are configured to communicate using an electromagnetic induction-based wireless communication technology. Inductive telemetry uses the mutual inductance established between two closely-placed coils. This type of telemetry is referred to as inductive telemetry or near-field telemetry because the coils must typically be closely situated for obtaining inductively coupled communication. An example inductive wireless communication technology utilizes an inductive coil in a first device (e.g., the external clinician device 120) which, if energized by an external voltage source, produces an inductive field that can be used to transmit communications signals and/or charging signals to a second device (e.g., the implantable device 104). The proximity necessary to use the inductive telemetry protocol provides enhanced security and allows active IMDs to transmit data and accept data from a device external to the body of the patient. In other embodiments, the implantable device 104, the external monitoring device 116 and/or the external clinician device 120 can employ infrared (IR) based communication technologies, ultrasonic based communication technologies, or microwave based communication technologies.

In various exemplary embodiments, the implantable device 104 can be configured to communicate different types of information with the external monitoring device 116 and the external clinician device 120. In particular, the implantable device 104 can establish a monitoring telemetry session 118 with the external monitoring device 116 and a clinician telemetry session 122 with the external clinician device 120. The nature, purpose and type of information communicated between the implantable device 104 and the external monitoring device 116 during a monitoring session and the implantable device 104 and the external clinician device 120 during a clinician session can vary. In general, a monitoring session 118 is employed by the implantable device 104 to communicate data captured and/or monitored by the implantable device 104 over the lifetime of the implantable device 104 (or since the last communication session) to an external monitoring device that is near the implantable device 104 (e.g., within a few feet or the same room). For example, the captured and monitored data can include physiological data associated with the body 102 and captured by the implantable device 104, therapy data associated with a therapy provided to the body 102 by the implantable device 104, operating information associated with operation of the implantable device 104, and the like. The information received by the external monitoring device 116 from the implantable device 104 can be processed by the external monitoring device 116 and/or relayed to a server device (shown and described below as server device 904 with reference to FIG. 9) and facilitate monitoring the health of the patient over time.

On the contrary, a clinician session 122 is generally employed to facilitate more invasive and on-demand or real-time communication between the implantable device 104 and an external clinician device 120. In particular, the external clinician device 120 can include a device operated by a caregiver or clinician of the patient. A clinician session 122 can be employed during interaction between the patient and the patient's caregiver or clinician, such as during scheduled office visits, during routine check-ups, during emergency situations, and the like. Using the external clinician device 120, the caregiver or clinician can establish a clinician session with the implantable device 104 to program or re-program an operating parameter of the implantable device 104, command the implantable device 104 to apply a therapy to the body, send the external clinician device 120 specific data captured by the implantable device 104 in real-time, send the external clinician device 120 specific data associated with the implantable device 104 that is only authorized for clinician use, and the like.

In various exemplary embodiments, the implantable device 104 can be configured to operate using different communication modes of operation or states to facilitate different features and functionalities associated with performing a monitoring session with an external monitoring device 116 and a clinician session with an external clinician device 120 using a commercially available RF-based telemetry communication technology (e.g., BLE or the like). For example, given the different sensitivities of information communicated between the implantable device 104 and an external clinician device 120 during a clinician session and communicated between the implantable device 104 and an external monitoring device 116 during a monitoring session, the implantable device 104 can employ different communication modes of operation for the respective external sessions that facilitate different levels of telemetry security. These different communication modes of operation can employ different telemetry communication technologies and protocols that facilitate the different levels of telemetry security. In addition, these different communication modes of operation can facilitate different amounts of transmitter and/or receiver activation and deactivation for facilitating the different types of data communication associated with a monitoring session and a clinician session (e.g., one-way communication, two-way communication, real-time communication, etc.). As a result, power consumption associated with performance of monitoring sessions and clinician sessions by the implantable device 104 is optimized and/or reduced.

In addition to facilitating different security levels and/or reducing power consumption associated with RF telemetry communication between the implantable device 104 and an external monitoring device 116 and between the implantable device 104 and an external clinician device 120, the implantable device 104 can be configured to employ different communication modes of operation in embodiments in which RF telemetry communication by the implantable device 104 is not needed or is unsafe. The implantable device 104 is further configured to operate using a non-RF-based telemetry communication protocol to enable telemetry communication between the implantable device 104 and the external monitoring device 116, the external clinician device 120, and/or another external device in these scenarios.

In one or more exemplary embodiments, the implantable device 104 can be configured to operate using a plurality of different communication modes of operation, including, but not limited to: a disabled mode, a monitoring session mode, a first advertising mode, a second advertising mode, a standby mode, and/or a clinician session mode. In various embodiments, one or more of the different communication modes of operation can facilitate a different telemetry functionality of the implantable device 104. For example, the disabled mode can be configured to ensure the implantable device 104 does not perform RF-based telemetry communication in a scenario in which RF-based communication is unnecessary, undesirable, or is unsafe. However, during the disabled mode, the implantable device 104 can be configured to enable telemetry communication using a non-RF-based telemetry communication technology/protocol, such as an induction-based telemetry communication technology/protocol. The first advertising mode can be configured to facilitate establishment of a monitoring telemetry session 118 between the implantable device 104 and the external monitoring device 116 using the RF-based telemetry communication protocol (e.g., BLE). The first advertising mode further restricts establishment of a monitoring session with the implantable device 104 to one or more external monitoring devices that the implantable device 104 has been previously programmed to consider authorized to establish a monitoring session with the implantable device 104. The monitoring session mode can be configured to support performance of a monitoring telemetry session established between the implantable device 104 and the external monitoring device 116 using the RF-based telemetry communication protocol.

The second advertising mode can be configured to facilitate establishment of a clinician telemetry session 122 between the implantable device 104 and the external clinician device 120 using the RF-based telemetry communication protocol. The second advertising mode further restricts establishment of a clinician session with the implantable device 104 to a single external clinician device that has current authority to establish the clinician session with the implantable device 104. The authority for a clinician session between the implantable device 104 and a particular external clinician device can be established at the time the particular external clinician device requests to establish the clinician session with the implantable device 104. This authority is further cleared or otherwise expires upon closing of the clinician session. The clinician session mode can be configured to support performance of an external clinician telemetry communication session established between the implantable device 104 and the external clinician device 120 using the RF-based telemetry communication protocol. The standby mode can be configured to facilitate reducing power consumption associated with performance of a clinician telemetry session during periods of reduced or paused telemetry communication activity between the implantable device 104 and the external clinician device 120. In some implantations, rather than employing a standby mode, the implantable device 104 is configured to remain in the clinician session mode yet modify an aspect of data transmission and/or reception by the implantable device to facilitate reducing power consumption by the implantable device. For example, the implantable device can remain in clinician session mode and prevent transmission of real-time data to the external clinician device 120 while enabling rapid bi-directional communication between the implantable device 104 and the external clinician device. In addition to operating using the various telemetry communication modes of operation described above, the implantable device 104 is further configured to intelligently determine if, how, and/or why to operate using the respective telemetry communication modes of operation over the lifetime of the implantable device 104 based on various defined conditions.

By employing the various communication modes of operation for operation of the implantable device 104, in one or more embodiments, medical device telemetry system 100 can employ a more robust security mechanism associated with establishing a clinician session with the implantable device 104 (e.g., which enables programming of the implantable device 104) relative to the security mechanism associated with generating a monitoring session with the implantable device 104 using an RF-based telemetry communication technology/protocol. In addition, medical device telemetry system 100 can facilitate rapid bi-directional and secure communication of sensitive data during a clinician session. Medical device telemetry system 100 can also facilitate minimizing battery consumption during a clinician session by employing a standby mode. Medical device telemetry system 100 can also facilitate minimizing battery usage/drain at times in embodiments in which the implantable device is not operating in the clinician session mode while enabling external monitoring. Furthermore, medical device telemetry system 100 can facilitate minimizing battery drain in embodiments in which a monitoring session and/or clinician session is not necessary via the disabled mode while still enabling telemetry communication with the implantable device 104 via a non-RF-based telemetry communication technology. Additional details of example embodiments of the subject telemetry communication modes of operation and telemetry communication mode management techniques are discussed in greater detail infra with respect to FIGS. 2-9.

It is to be appreciated that the implantable device 104 can include one or more devices, transducers and/or circuits that can facilitate telemetry communication and disablement of telemetry communication in accordance with one or more of the telemetry communication technologies described above. For example, the implantable device 104 can include an RF transmitter that transforms electrical power into a signal associated with transmitted data packets. Additionally, the implantable device 104 can include one or more RF devices, transducers and/or circuits that can facilitate receiving information from one or more devices (e.g., the external monitoring device 116, the external clinician device 120, etc.).

For example, the implantable device 104 can include an RF receiver that transforms a signal into electrical power. The implantable device 104 can also include hardware, software, or a combination of hardware and software that can facilitate non-RF-based telemetry communication technologies and protocols. For example, the implantable device 104 can include an induction antenna and associated circuitry that can facilitate receiving and interpreting induction-based signals and generating and transmitting induction-based signals.

In various embodiments, the implantable device 104 can include any number of different types of implantable devices configured to communicate with the external monitoring device 116, the external clinician device 120, or another external device. The particular, size, shape, placement and/or function of the implantable device 104 may not be critical to the subject disclosure in some embodiments. In one embodiment, as mentioned, the implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the implantable device 104 can be or include any number of other types of implantable devices that are not IMDs.

For exemplary purposes, the implantable device 104 is illustrated in medical device telemetry system 100 as an IMD implanted within the chest of a patient and configured to provide medical treatment or therapy associated with a heart disease or condition (e.g., an implantable cardioverter-defibrillator (ICD) and/or a pacemaker). In addition to the medical treatment, the implantable device 104 can also be configured to provide the data packetizing and communication operations described herein. The implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component. The various embodiments described herein can provide improved management of power associated with the one or more power sources.

The electrical components can vary depending on the particular features and functionality of the implantable device 104. In various embodiments, these electrical component can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the implantable device 104 is also an IMD and further includes leads 110*a,b* connected to the housing 106. The leads 110*a,b* extend into the heart and respectively include one or more electrodes. For example, as depicted in medical device telemetry system 100, leads 110a,b each include a respective tip electrodes 112a,b and ring electrodes 114a,b located near a distal end of their respective leads 110a,b. In embodiments in which implanted, tip electrodes 112a,b and/or ring electrodes 114a,b are placed relative to or in a selected tissue, muscle, nerve or other location within the body 102 of the patient. As depicted in medical device telemetry system 100, tip electrodes 112a,b are extendable helically shaped electrodes to facilitate fixation of the distal end of leads 110a,b to the target location within the body 102 of the patient. In this manner, tip electrodes 112a,b are formed to define a fixation mechanism. In other embodiments, one or both of tip electrodes 112a,b may be formed to define fixation mechanisms of other structures. In other instances, leads 110a,b may include a fixation mechanism separate from tip electrodes 112a,b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a,b are connected at a proximal end of the implantable device 104 via connector block 108. Connector block 108 may include one or more receptacles that interconnect with one or more connector terminals located on the proximal end of leads 110a,b. Leads 110a,b are ultimately electrically connected to one or more of the electrical components within housing 106. One or more conductors (not shown) extend within leads 110a,b from connector block 108 along the length of the lead to engage the ring electrodes 114a,b and tip electrodes 112a,b, respectively. In this manner, each of tip electrodes 112a,b and ring electrodes 114a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors may electrically couple to circuitry, such as a therapy module or a sensing module, of the implantable device 104 via connections in connector block 108. In one or more embodiments, the implantable device 104 can be configured to deliver therapy to the heart (or other location) via the electrical conductors to one or more of electrodes 112a and 112b and 114a and 114b. In the case of pacing therapy, for example, therapy circuitry within the implantable device 104 can generate and deliver pacing pulses via a unipolar electrode configuration, e.g., using electrodes 112a and 112b and a housing electrode of the implantable device 104. In other instances, the therapy circuitry within the implantable device 104 can deliver pacing pulses via a bipolar electrode configuration, e.g., using electrodes 112a and 112b and ring electrodes 114a and 114b. The therapy circuitry may include one or more pulse generators, capacitors, and/or other components capable of generating and/or storing energy to deliver as pacing therapy in accordance with a pacing regime stored within memory.

Implantable device 104 can also receive sensed electrical signals on the electrical conductors from one or more of electrodes 112a and 112b and 114a and 114b. The implantable device 104 can sense the electrical signals using either a unipolar or bipolar electrode configuration. Sensing circuitry of the implantable device 104 may process the sensed electrical signals and the implantable device 104 may analyze the processed and/or or sensed electrical signals and provide the pacing as a function of the sensed electrical signal. The sensing circuitry may include one or more sense amplifiers, filters, rectifiers, threshold detectors, comparators, analog-to-digital converters (ADCs), or other analog or digital components.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In other embodiments, the lead may be an extravascular lead with the electrodes implanted subcutaneously above the ribcage/ sternum or substernally underneath or below the sternum. Example extravascular ICDs having subcutaneous electrodes are described in U.S. Patent Publication No. 2014/ 0214104 (now U.S. Pat. No. 9,072,914) (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing, (e.g., defibrillation or cardioversion), the leads can include elongated electrodes, which may, in some instances take the form of a coil. The therapy circuitry of the implantable device 104 can generate and deliver defibrillation or cardioversion shocks to the heart via any combination of the elongated electrodes and housing electrode. The therapy circuitry may include one or more high voltage (HV) output capacitors and a HV charging circuit, which may include one or more capacitors, resistors, inductors, transformers, switches, or other analog or digital components, and discharging circuitry to deliver cardioversion or defibrillation therapy, including, for example, an H-bridge circuit. In another embodiment, the implantable device 104 can include leads with a plurality of ring electrodes, (e.g., as used in some implantable neurostimulators), without a tip electrode or with one of the ring electrodes functioning as the "tip electrode."

In another embodiment, the implantable device 104 may include no leads, as in the case of an intracardiac pacemaker or a leadless pressure sensor. In the case of an intracardiac pacemaker, the device may include a housing sized to fit wholly within the patient's heart. In one example, the housing may have a volume that is less than 1.5 cc and, more preferably, less than 1.0 cubic centimeter (cc). However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (now U.S. Pat. No. 8,386,051) (Kenneth), and U.S. Patent Publication No. 2014/0214104 (now U.S. Pat. No. 9,072,914) (Greenhut et al.), each of which is incorporated herein in its entirety. In the case of a leadless pressure sensor, the device can include a housing having a fixation member and a pressure sensing component. One example of a leadless pressure sensor is described in U.S. Patent Publication No. 2012/0108922 (now U.S. Pat. No. 8,475,372) (Schell et al.), which is incorporated herein in its entirety.

External monitoring device 116 and/or external clinician device 120 can include any suitable computing device configured to communicate with implantable device 104. In some embodiments, the external monitoring device 116 and/or the external clinician device 120 can be an external electronic device. For example, external monitoring device 116 and/or the external clinician device 120 can include, but are not limited to, a handheld computing device, a mobile phone, a smart phone, a tablet personal computer (PC), a laptop computer, a desktop computer, a personal digital assistant (PDA) and/or a wearable device. In some embodiments, the external monitoring device 116 and/or the external clinician device 120 can include a display that can present information associated with the implantable device 104. In another embodiment, the external monitoring device 116 and/or the external clinician device 120 can include an application and/or a program associated with the implantable device 104. Still in yet another embodiment, one or more features and functionalities of external monitoring device 116 and external clinician device 120 can be provided on a single computing device. According to this embodiment, the single computing device can be configured to operate in an external monitoring capacity and an external clinician capacity depending on the context and application of the computing device.

Figure 2:
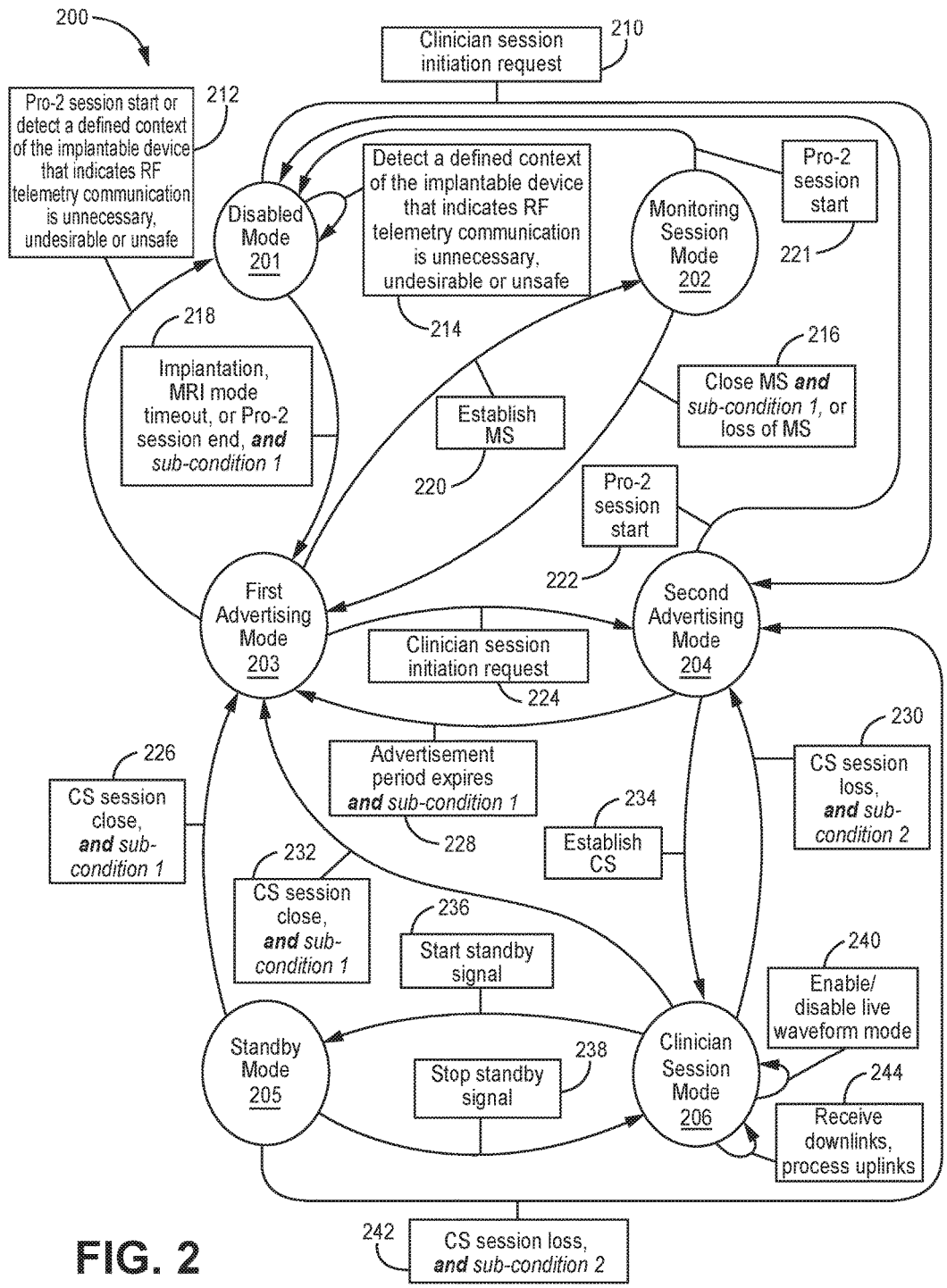
FIG. 2 illustrates an example, non-limiting state diagram for an implantable device in accordance with one or more embodiments described herein.

FIG. 2 illustrates an example, non-limiting state diagram 200 for an implantable device (e.g., implantable device 104) in accordance with one or more embodiments described herein. Repetitive description of like elements employed in respective embodiments described herein is omitted for sake of brevity.

The state diagram 200 depicts six dedicated communication modes of operation for the implantable device 104, including a disabled mode 201, a monitoring session mode 202, a first advertising mode 203, a second advertising mode 204, a standby mode 205 and a clinician session mode 206. Each (or, in some embodiments, one or more) of the different communication modes of operation can facilitate a different telemetry functionality of the implantable device (e.g., implantable device 104).

For example, the disabled mode 201 can be an operational mode of the implantable device wherein RF-based telemetry communication of the implantable device is disabled or prevented via deactivation of an RF transmitter/receiver or transceiver of the implantable device. However, telemetry communication via a non-RF telemetry communication technology of the implantable device 104 (e.g., induction) can be enabled during the disabled mode, thereby allowing optional communication with the implantable device (e.g., using a proprietary telemetry communication protocol or near field communication protocol, generally). The disabled mode 201 can be configured to ensure the implantable device does not perform RF-based telemetry communication in defined scenarios or contexts of the implantable device in which RF-based communication is unnecessary, desirable, and/or unsafe, thereby minimizing power consumption associated with activation of one or more RF components of the implantable device and minimizing the opportunity for non-authorized external device to attempt to communicate with the implantable device (e.g., read data from the implantable device or program the implantable device) using a commercially available RF telemetry communication protocol (e.g., BLE). For example, the implantable device can be configured to operate using the disabled mode 201 before it is implanted into the body of a patient, thereby reducing power consumption associated with activation of one or more RF components of the implantable device before the implantable device is implanted. In addition, the disabled mode 201 can provide for reduced power consumption associated with activation of one or more RF components of the implantable device after the implantable device is implanted into a patient when RF telemetry is not needed or is unsafe. For example, in one or more embodiments, the implantable device can operate using the disabled mode if the patient is undergoing medical procedures that RF components of the implantable device can hinder if activated (e.g., magnetic medical imaging procedures). In another example, in one or more embodiments, after implantation, the implantable device can operate using the disabled mode 201 if an authorized external device (e.g., external clinician device 120, external monitoring device 116, or another external device) is communicating with the implantable device using a non-RF-based telemetry communication protocol. Still in yet another embodiment, after implantation, the implantable device can operate using the disabled mode 201 if the implantable device is not performing or facilitating performance of a clinician session (e.g., with external clinician device 120) and if the implantable device is not scheduled to perform a monitoring session (e.g., with external monitoring device 116).

The first advertising mode 203 can facilitate establishment of a monitoring telemetry session between the implantable device and an external monitoring device. During the first advertising mode 203, the implantable device can activate one or more RF components of the implantable device (e.g., an RF transmitter, an RF receiver, or an RF transceiver) in accordance with a defined RF telemetry communication protocol employed by the implantable device for the first advertising mode (e.g., BLE). The implantable device can further transmit one or more advertisement data packets according to the defined RF telemetry communication protocol, and receive one or more responses to the advertisement data packets. The implantable device can further determine if the one or more responses are received from an authorized external monitoring device (e.g., external monitoring device 116) and request establishment of a defined monitoring session between the authorized external monitoring device and the implantable device. The implantable device can further communicate with the authorized external monitoring device to set up or establish the authorized monitoring session.

The monitoring session mode 202 can support performance of external monitoring telemetry sessions established between the implantable device and an external monitoring device (e.g., external monitoring device 116). In one or more embodiments, during the monitoring session mode 202, the implantable device performs RF telemetry communication with an authorized external monitoring device according to defined communication parameters for the monitoring session. For example, the implantable device can send the external monitoring device physiological information that the implantable device previously obtained about the patient. In another example, the implantable device can send the external monitoring device operating performance information monitored by the implantable device.

The second advertising mode 204 can be configured to facilitate establishment of a clinician telemetry session between the implantable device and an external clinician device (e.g., external clinician device 120). During the second advertising mode, the implantable device can activate one or more RF components of the implantable device (e.g., an RF transmitter, an RF receiver, or an RF transceiver) in accordance with a defined RF telemetry communication protocol employed by the implantable device for the second advertising mode (e.g., BLE). For example, the bi-implantable device can further transmit one or more advertisement data packets according to the defined RF telemetry communication protocol, and receive one or more responses to the advertisement data packets. The implantable device can further determine if the one or more responses are received from an authorized external clinician device (e.g., external clinician device 120) and request establishment of a defined clinician session between the authorized external clinician device and the implantable device. The implantable device can further communicate with the authorized external clinician device to set up or establish the authorized clinician session.

The clinician session mode 206 can support performance of external clinician telemetry communication sessions established between the implantable device and an external clinician device. For example, in one or more embodiments, during the clinician session mode 206, the implantable device performs RF telemetry communication with an authorized external clinician device according to defined communication parameters for the clinician session. For instance, the external clinician device can send the implantable device programming or command information for application by the implantable device. In another example, the implantable device can send the external clinician device information requested by the external clinician device. In one or more embodiments, during the clinician session mode 206, the authorized external clinician device can command the implantable device to operate in a waveform mode in which the implantable device sends the external clinician device waveform data (e.g., live waveform data) captured by the implantable device.

The standby mode 205 can facilitate reducing power consumption associated with performance of a clinician telemetry session during periods of reduced or paused telemetry communication activity between the implantable device and the external clinician device. In one or more embodiments, during the standby mode 205, the implantable device maintains a clinician session telemetry connection (e.g., connection 122) with an authorized external clinician device, and reduces an amount of RF component activation and usage relative to the amount of RF component activation and usage employed by the implantable device during the clinician session mode 206. For example, in some embodiments, the implantable device can activate the implantable device transmitter to occasionally (e.g., once every few seconds) send one or more idle data packets to the external clinician device with idle information that informs the clinician device that the implantable device is available to communicate with the clinician device in accordance with the parameters and protocols defined for the established external clinician telemetry session. After sending the one or more idle packets, the implantable device can activate the implantable device receiver for a defined duration of time (e.g., one second) to allow for reception of a request, from the clinician device, to exit the standby mode 205 and re-enter clinician session mode 206. Between transmission of the one or more idle packets, the implantable device can operate in a sleep mode wherein the implantable device temporarily deactivates its receiver and transmitter. In some implantations, rather than employing standby mode 205, the implantable device is configured to remain in the clinician session mode 206 yet modify an aspect of data transmission and/or reception by the implantable device to facilitate reducing power consumption by the implantable device. For example, the implantable device can remain in the clinician session mode 206 and prevent transmission of real-time data to the external clinician device while enabling rapid bi-directional communication between the implantable device and the external clinician device.

The implantable device can transition between operating in these respective communication modes of operation over the lifespan of the implantable device. The implantable device is generally configured to operate using one of the six communication modes of operation at a time, however in some embodiments, the implantable device can operate in two or more of the six communication modes of operation concurrently. Usage of the different communication modes of operation over the course of operation of the implantable device can facilitate extension of the lifespan of a power source of the implantable device, can provide efficient telemetry communication of different types of information between the implantable device and one or more external devices, and can enhance security of telemetry communication of different types of information between the implantable device and one or more external devices.

The various arrow lines connecting one communication mode to another communication mode can identify a path via which the implantable device can transition between the respective communication modes of operation. The numerated boxes associated with the respective arrow lines respectively define a transition event that can cause the implantable device to transition from one communication mode to another communication mode in the direction of the arrow line with which the transition event is associated.

With reference initially to disabled mode 201, the implantable device can be generally received (e.g., from the manufacturer of the implantable device) by a clinician or other suitable medical caregiver or technician in the disabled mode 201. In accordance with one or more embodiments, the implantable device can be configured to perform telemetry communication using at least a first telemetry communication technology/protocol and a second telemetry communication technology/protocol, including at least one RF-based telemetry communication technology/protocol. For example, the implantable device can be configured to operate using an induction-based telemetry communication technology/protocol and a BLE technology/protocol, an NFC technology/protocol, a Wi-Fi technology/protocol, etc. In another example, the implantable device can be configured to operate using an acoustic based telemetry communication technology protocol and a BLE technology/protocol. In another example, the implantable device can be configured to operate using an NFC technology protocol and a BLE technology/protocol. For exemplary purposes, state diagram 200 is described wherein the implantable device employs BLE as a first telemetry communication approach and an induction-based telemetry communication as a second telemetry communication approach.

In embodiments in which the implantable device is operating in disabled mode 201, the implantable device can be configured to deactivate telemetry communication according to the first telemetry communication technology/protocol and activate or enable telemetry communication according to the second telemetry communication technology/protocol. For example, while in disabled mode 201, the implantable device can deactivate or disable the wireless adapter, RF transmitter, RF receiver and/or RF transceiver employed by the implantable device to conduct telemetry communication using the first telemetry communication technology/protocol. However, during disabled mode 201, the implantable device can enable or activate reception and/or transmission of an inductive current based telemetry signal by the implantable device (e.g., via an induction coil/antenna and associated circuitry of the implantable device).

The implantable device can be configured to remain in disabled mode 201 upon and/or during the occurrence of a transition event 214, which includes a defined context of the implantable device that indicates RF telemetry communication is unnecessary, undesirable or unsafe for use by the implantable device. For example, in one implementation, once in disabled mode 201, the implantable device can be configured to remain in disabled mode upon and/or during establishment and performance of a telemetry communication session between the implantable device and an external device (e.g., external monitoring device 116, external clinician device 120, and/or another external device) using the second telemetry communication technology/protocol, referred to in state diagram 200 and the like as a protocol-2 (Pro-2) session. The implantable device can also be configured to remain in disabled mode 201 if the implantable device detects that it is not implanted or partially implanted within the body of a patient. The mechanism via which the implantable device can determine implantation can vary based on the features and functionalities of the implantable device. In one implementation, in embodiments in which the implantable device includes an ICD or pacemaker, for example, the implantable device can determine whether the implantable device is implanted or not implanted in a body primarily based on lead impedance measurements (e.g., leads 110a,b of implantable device 104). According to this implementation, the implantable device can capture lead impedance measurements (e.g., on every paced beat). If the implantable device has not been implanted within a patient (e.g., when initially received from the manufacturer), there will be no leads connected to the heart so the lead impedance measurements will be high. As soon as both the atrial and right ventricular unipolar lead impedance measurements are within a defined normal range, the implantable device assumes that the implantable device has been connected to the leads and is implanted in the body. This determination can trigger the implantable device to start recording diagnostic data.

The implantable device can also be configured to remain in disabled mode 201 upon and/or during activation of magnetic resonance imaging (MRI) mode, such as MRI SureScan™ mode offered in commercially available MRI-conditional devices from Medtronic, PLC. As used herein, "MRI" mode refers to an operating mode of the implantable device that can facilitate performing magnetic imaging (e.g., magnetic resonance imaging (MRI)) of a patient in which the implantable device is implanted without causing physical harm to the patient or the implantable device. For example, if one or more RF components of the implantable device are activated during an MRI procedure, the magnet and RF energy of the MRI machine can affect the RF components in the implantable device. The MRI mode is also referred to herein as a magnetic imaging mode. In an embodiment in which MRI mode is enabled, the one or more RF components (e.g., transmitter and/or receiver) of the implantable device can be deactivated to prevent undesirable interactions between the RF components of the device and the MRI machine. In various implementations, MRI mode can be enabled and disabled by an external device (e.g., external clinician device 120 or another external device) while the implantable device 104 is in disabled mode 201 as well as other modes (e.g., monitoring session mode 202, clinician session mode 206, etc.) via provision of a MRI mode enablement or disablement signal to the implantable device using either the first telemetry communication technology/protocol or the second telemetry communication protocol/technology. In some embodiments, the implantable device can be configured to automatically remain in or enter disabled mode from another mode based on detecting the presence of an MRI device (e.g., a large static magnetic field). In various embodiments, the implantable device can be configured to enter disabled mode 201 from another communication mode upon activation of MRI mode. Further, once in disabled mode 201, the implantable device can be configured to remain in disabled mode if a remote monitoring functionality of the implantable device is disabled. The remote monitoring functionality of the implantable device refers to a programmable condition of the implantable device. If the implantable device will be used to perform in coordination with an external monitoring device (e.g., external monitoring device 116) to perform monitoring telemetry sessions, the implantable device can be programmed for 'external monitoring enabled.' If the implantable device will not be used in coordination with an external monitoring device, the implantable device can be programmed for 'external monitoring disabled.' This is typically a one time programming action and may or may not change over time in various different embodiments. In one or more embodiments, programming of the implantable device to either an external monitoring enabled or an external monitoring disabled mode can be performed via an external clinician device (e.g., external clinician device 120) using a wired or wireless telemetry communication protocol.

The implantable device can be configured to transition from the disabled mode 201 to either the first advertising mode 203 or the second advertising mode 204. During the first advertising mode 203 and the second advertising mode 204, the implantable device activates telemetry communication using the first telemetry communication technology/protocol. For example, in an embodiment in which the first telemetry communication technology/protocol is BLE or another RF technology, the implantable device can activate or enable the BLE wireless adapter, RF transmitter, RF receiver and/or RF transceiver of the implantable device employed to perform telemetry. Following activation, an RF transmitter of the implantable device then can transmit advertisement data packets according to defined advertisement data packet signaling parameters for the first advertising mode 203 and the second advertising mode 204. For example, in accordance with various short range communication protocols that can be employed for RF telemetry communication between two devices (e.g., BLE communication protocol), the implantable device can transmit advertisement data packets according to a defined schedule (e.g., once every few seconds, once every minute, once every three minutes, etc.) or in response to a trigger event. As used herein, the advertisement signals or packets can also include beacon signals in some embodiments. The advertisement data packets or signals can include information indicating the implantable device is ready or available to communicate with an external device. An external device (e.g., external monitoring device 116 and/or external clinician device 120) actively employing the first telemetry communication technology/protocol (e.g., BLE) can be configured to detect or receive advertisement signals transmitted by the implantable device. Reception of an advertisement signal by an external device from the implantable device is referred to herein as a "discovery event."

The implantable device can be configured to establish a telemetry communication session with an external device (e.g., external monitoring device 116, external clinician device 120, or another external device) based in part on reception of an advertisement data packet from the implantable device. For example, in accordance with BLE telemetry communication protocol, after an external device receives an advertisement data packet from an implantable device, the external device can send a connection request to the implantable device requesting establishment of a telemetry communication session with the implantable device. The implantable device can then respond to the connection request and establish a telemetry session with the external device.

In addition to establishing a telemetry session with an external device (e.g., external monitoring device 116, external clinician device 120, and/or another external device) based on reception, by the external device, of an advertisement signal transmitted by the implantable device, the implantable device can be configured to establish the telemetry session with the external device based on a determination that the external device is authorized to establish the telemetry session. In particular, the information communicated between an IMD and an external device using telemetry is often highly sensitive and personal. As commercially available telemetry protocols (e.g., BLE) are employed to perform telemetry with an implantable device, the knowledge of how to initiate and conduct a telemetry session with the implantable device can become publicly available. For example, in an embodiment in which BLE is employed by the implantable device to perform telemetry, an unauthorized device can detect an advertisement signal transmitted by the implantable device and attempt to establish a telemetry session with the implantable device. Accordingly, the implantable device can be configured to employ one or more security mechanisms in order to determine that an external device that received an advertisement data packet transmitted by the implantable device (e.g., during the first advertising mode 203 or the second advertising mode 204) is authorized to establish a telemetry session with the implantable device.

In various embodiments, the implantable device can be configured to employ the first advertising mode 203 to facilitate a first type of telemetry communication session with an external device (e.g., external monitoring device 116 and/or external clinician device 120) and the second advertising mode 204 to facilitate a second type of telemetry communication session with an authorized device (e.g., external monitoring device 116 and/or external clinician device 120). The first type of telemetry communication session includes a monitoring session, (identified in state diagram 200 as MS), and the second type of telemetry communication session includes a clinician session (identified in state diagram 200 as CS). An external device authorized to establish a monitoring session with the implantable device is referred to herein as an external monitoring device (e.g., external monitoring device 116) and an external device authorized to establish a clinician session with the implantable device is referred to herein as an external clinician device (e.g., external clinician device 120).

The nature, purpose and type of information communicated between the implantable device and an external device during a monitoring session and a clinician session can vary. In particular, data communication during a monitoring session can be more restrictive (e.g., read only) than data communication during the clinician session (e.g., read and program). For example, in accordance with one or more embodiments, the implantable device can establish and perform a monitoring session with an external monitoring device in order to transmit or report information monitored by the implantable device over the course of implantation and operation within a patient. For example, the implantable device can be configured to capture (periodically, randomly or otherwise) physiological information about a patient implanted with the implantable device and transmit the physiological information to an external monitoring device (e.g., external monitoring device 116). The external monitoring device can include a device associated with the patient implanted with the implantable device, such as smartphone or a tablet, that is carried by the patient or otherwise located within wireless transmission range of the implantable device on a regular basis (e.g., throughout the day, while the patient is home, while the patient is sleeping etc.). The implantable device can be configured to establish a monitoring session once a day, a few times a day, once an hour, once a week, every other week, in response to detection of specific triggering physiological information, etc. Telemetry communication between the implantable device and the external monitoring device during a monitoring session substantially involves one-way communications transmitted from the implantable device to the external monitoring device. In many implementations, telemetry communication during a monitoring session involves little or no reception of programming or configuration or re-configuration information by the implantable device from the external monitoring device.

On the contrary, in various embodiments, a clinician session can be configured to facilitate rapid one-way or two-way communication between the implantable device and an external clinician device (e.g., external clinician device 120). For example, a clinician session can be initiated by a medical clinician or caregiver (e.g., a doctor, a nurse, a medical technician, a mother, etc.) authorized to care for the patient implanted with the implantable device using an authorized external clinician device. The clinician session can be employed during an in-office, in-hospital, or otherwise in-person meeting between the patient and the medical clinician to perform more sophisticated, critical or intrusive data communication between the implantable device and the external clinician device relative to the data communication associated with a monitoring session. For example, in addition to reading or receiving data monitored by the implantable device, a clinician session can be used to send programming information by the external clinician device to the implantable device that is employed by the implantable device to program or re-configure one or more operating parameters of the implantable device (e.g., a frequency of physiological sensing, a dosage of a therapeutic drug supplied by the implantable device, etc.). In another example, a clinician session can be employed to direct the implantable device to capture certain types of data on demand and report the data in real-time to the external clinician device (e.g., electrocardiogram waveform data). In another example, a clinician session can be employed to direct the implantable device to perform certain functions on demand (e.g., drug delivery, therapy application, etc.).

As noted above, the first advertising mode 203 can facilitate establishment of a monitoring session between the implantable device and an external monitoring device (e.g., external monitoring device 116) and the second advertising mode 204 can facilitate establishment of a clinician session between the implantable device and an external clinician device (e.g., external clinician device 120). Given the different sensitivities of information communicated between the implantable device and an external clinician device during a clinician session and the implantable device and an external monitoring device during a monitoring session, the second advertising mode 204 can be configured to employ heightened security measures relative to the security measures employed by the first advertising mode 203. Based on the different security measures associated with the second advertising mode 204 and the first advertising mode 203, in various embodiments, the implantable device can only establish a monitoring session with an authorized external monitoring device (e.g., external monitoring device 116) from the first advertising mode 203 and a clinician session with an authorized external clinician device (e.g., external clinician device 120) from the second advertising mode 204.

In addition, the first advertising mode 203 and the second advertising mode 204 can be tailored to employ different communication parameters and security measures to account for these differences in the types of telemetry communication sessions respectively supported. For example, the number, frequency and/or timing of advertisement data packets to be transmitted by the implantable device while operating in the first advertising mode 203 and the second advertising mode 204 can be tailored to facilitate monitoring sessions and clinician sessions, respectively. Information included in the respective advertisement data packets can also vary based on the applications of the implantable device in association with the first advertising mode 203 and the second advertising mode 204. For example, in one implementation, the frequency of transmission of advertisement data packets in the second advertising mode 204 is higher than the frequency of transmission of advertisement data packets in the first advertising mode 203. For instance, during the second advertising mode, the implantable device can be configured to transmit advertisement data packets at a rate of about one advertisement data packet per second. As a result, an external device (e.g., external clinician device 120) can quickly discover the implantable device and establish and/or re-establish (e.g., in response to unintentional loss) a telemetry session with the implantable device. Quick establishment and re-establishment of a telemetry session with an implantable device can improve the likelihood of efficient and consistent data transfer between the implantable device and the external device, a characteristic that is generally more critical in the clinician session context relative to monitoring session context. On the other hand, during the first advertising mode, the implantable device can transmit advertisement data packets at a lower rate, such as one advertisement data packet every three minutes. In some implementations, during the first advertising mode, the implantable device can be configured to transmit advertisement data packets during only certain period of the day. As a result, current drain associated with transmitter and receiver activation in association with transmitting advertisement signals and waiting for a response can be reduced and/or minimized.

In another implementation, the implantable device can be configured to transmit advertisement data packets in association with an "advertising session." According to this implementation, an "advertising session" involves the transmission of advertisement data packets by the implantable device at a rate of N advertisement data packets every M milliseconds (ms). For example, the advertisement rate in this implementation can include 3 advertisement data packets every 80 ms. With this implementation, the implantable device can transmit advertisement data packets at the same rate (e.g., 3 packets/80 ms) during the first and second advertising modes, yet employ different durations for the respective advertising sessions. For example, the duration of the advertising session during the first advertising mode 203 can be much shorter (e.g., 480 ms) than the duration of the advertising session employed by the implantable device during the second advertising mode 204 (e.g., 5 minutes). In addition, during the first advertising mode 203, the implantable device can be configured to perform an advertising session according to a defined protocol (e.g., at a rate of 3 packets/80 ms for a duration of 480 ms) at a low frequency (e.g., one advertising session every three minutes). On the contrary, in various embodiments, the implantable device is configured to perform an advertising session in association with operating in the second advertising mode 204 only and immediately in response to entering the second advertising mode (e.g., based on reception of a clinician session initiation request). The implantable device can further be configured to conduct an advertising session according to a defined protocol (e.g., at a rate of 3 packets/80 ms) for the entire duration during which the implantable device operates in the second advertising mode 204.

With reference back to state diagram 200, transition event 218 identifies some example transition events that can cause the implantable device to transition from the disabled mode 201 to the first advertising mode 203. In one or more embodiments, the implantable device can be configured to transition from the disabled mode 201 to the first advertising mode 203 in response to implantation detection, MRI mode time out, or ending of a protocol-2 telemetry session, and satisfaction of sub-condition 1. Sub-condition 1 refers to a defined context of the implantable device that renders usage of the first type of telemetry communication protocol (e.g., an RF based telemetry communication protocol) by the implantable device necessary, desirable, or safe. In one or more embodiments, sub-condition 1 can include three conditions that must be satisfied in addition to the occurrence of one of the transition events identified by transition event 218 in order for the implantable device transition from the disabled mode 201 to the first advertising mode 203. These three conditions include MRI mode being disabled, implantation being detected, and external monitoring being enabled. If sub-condition 1 is not satisfied, the implantable device can remain in disabled mode 201. For example, while in disabled mode 201 and the implantable device detects implantation, the implantable device can remain in disabled mode if MRI is enabled or external monitoring is disabled. In another example, while in disabled mode 201 and the implantable device detects a MRI mode timeout, the implantable device can then remain in disabled mode if MRI mode is still enabled or external monitoring is disabled. In another example, while in disabled mode 201 and the implantable device determines that a protocol-2 telemetry session is established between the implantable device and an external device (e.g., external monitoring device 116, external clinician device 120, or another external device), the implantable device can remain in disabled mode if MRI mode is enabled, implantation is not detected, or external monitoring is disabled.

Transition event 210 identifies an example transition event that causes the implantable device to transition from disabled mode 201 to the second advertising mode; a clinician session initiation request. A clinician session initiation request refers to a request received by the implantable device from an external device (e.g., external clinician device 120) to perform a clinician session with the implantable device using the first telemetry communication protocol (e.g., BLE). In one embodiment, a clinician session initiation request is also the transition event that causes the implantable device to transition from the first advertising mode 203 to the second advertising mode 204, as indicated via transition event 224. Accordingly, in the embodiment depicted in by state diagram 200, the only way the implantable device can enter into the second advertising mode 204 is in response to reception of a clinician session initiation request. Further, in the embodiment shown, the only way the implantable device can establish a clinician session and operate in the clinician session mode 206 is via transition from the second advertising mode 204.

The clinician session initiation request can facilitate an enhanced security mechanism for ensuring or increasing the likelihood that only an authorized device can establish a clinician session with the implantable device using the first telemetry communication protocol/technology (e.g., BLE). In one or more embodiments, the implantable device is configured to not receive a clinician session initiation request from an external device via the first telemetry communication protocol. On the contrary, the implantable device employs the second telemetry communication protocol (or a third telemetry communication protocol) to receive clinician session initiation requests. The secondary telemetry communication protocol can be considered more secure than the first telemetry communication protocol. For example, in an embodiment in which the second telemetry communication protocol includes an induction-based telemetry communication protocol, only external devices configured to employ the induction-based telemetry communication protocol can send a clinician session initiation request to the implantable device. The proximity necessary to use the inductive telemetry protocol provides an enhanced level of security. In another example, the second telemetry communication protocol includes a proprietary (e.g., not commercially available) telemetry communication protocol. Thus, while operating in disabled mode 201 and first advertising mode 203, the implantable device can be configured to enable telemetry communication via the second telemetry communication technology/protocol, thereby enabling reception of a clinician session initiation request.

The implantable device can be configured to interpret a clinician session initiation request received from an external clinician device (e.g., external clinician device 120) via the second telemetry communication protocol/technology as a request to establish a clinician session with the implantable device using the first telemetry communication technology/protocol. In one embodiment, a clinician session initiation request can include identification information for the external clinician device that is required to establish the clinician session with the implantable device. In one or more embodiments, the identification information includes at least an identifier for the external clinician device. For example, the identifier for the external clinician device can include a radio frequency module (RFM) address of the external clinician device, a media access control (MAC) address for the external clinician device, or any other value.

In response to reception of a clinician session initiation request, the implantable device can generate unique time sensitive authorization information that, in one embodiment, is required for the establishment of the requested clinician session between the implantable device and the external clinician device. This time sensitive authorization information can be employed to establish the currently requested clinician session. For example, after a clinician session established between the implantable device and the external clinician device using the authorization information is closed, the implantable device clears the authorization information from memory (e.g., deletes or otherwise treats as expired). In addition, if the implantable device and the external clinician device fail to establish a clinician session using the authorization information within a defined window of time (e.g., the advertisement period), the implantable device clears the authorization information from memory (e.g., deletes or otherwise treats as expired). As a result, in order for the same external clinician device to establish a new clinician session with the implantable device, in some embodiments, the external clinician device will have to send a new clinician session initiation request to the implantable device and the implantable device will have to generate new authorization information.

In an exemplary embodiment, the time sensitive authorization information includes a dynamically generated unique session identifier including random numbers (e.g., a universal unique identifier (UUID) or the like). The time sensitive authorization information can also include one or more dynamically generated unique session keys (e.g., an advanced encryption standard (AES) key or the like). For example, the implantable device can generate a unique application layer encryption key (e.g., a 128 bit application layer encryption key) and unique link layer encryption key (e.g., a 128 bit link layer encryption key). The one or more unique session keys can be employed by the implantable device and the external clinician device to encrypt and decrypt information communicated between the respective devices during the clinician session. The implantable device can be configured to generate the unique time sensitive authorization information (e.g., the unique session identifier and the one or more session keys) in response to reception of the clinician session initiation request. Accordingly, the authorization information is not previously known or available to any device, including the implantable device and the external clinician device. The implantable device can be further configured to send the dynamically generated time sensitive authorization information to the clinician device via an information signal formatted and sent to the clinician device using the second telemetry communication technology/protocol. For example, in an embodiment in which the second telemetry communication technology/protocol includes an induction-based protocol, the implantable device can be configured to send the authorization information to the clinician device using an induction-based telemetry communication signal. After the implantable device sends the authorization information to the requesting external clinician device using the second telemetry communication technology/protocol, the implantable device can begin operating in the second advertising mode 204. In one or more implementations, while operating in the second advertising mode, the implantable device can generate and transmit one or more advertisement data packets that indicate the availability of the implantable device to establish a telemetry session using the first telemetry communication protocol. The one or more advertisement data packets respectively include the unique session identifier (e.g., a UUID) generated by the implantable device in response to reception of the clinician session request and provided to the external clinician device using the second telemetry communication technology/protocol.

Once the implantable device is operating in the second advertising mode 204, the implantable device can transition to the clinician session mode 206 or back to the first advertising mode 203 or the disabled mode 201. As identified by transition event 234, the implantable device can be configured to transition from the second advertising mode 204 to the clinician session mode 206 based on establishment of a clinician session with an authorized external clinician device. The implantable device can establish and conduct the clinician session using the first telemetry communication technology/protocol (e.g., BLE). In one or more embodiments, if the implantable device establishes a clinician session with an authorized external clinician device, the implantable device can disable telemetry communication by the implantable device using the second telemetry communication technology/protocol. For example, the implantable device can disable induction-based telemetry communication by the implantable device.

The implantable device can establish a clinician session with an authorized external clinician device based on reception of a clinician session connection request from an authorized external clinician device while operating in the second advertising mode 204. In some implementations, the device with which the implantable device is authorized to establish a clinician session is the specific external clinician device that caused the implantable device to enter into the second advertising mode 204 via the clinician session initiation request transmitted to the implantable device using the second telemetry communication technology/protocol (e.g., induction-based telemetry). In particular, after the implantable device begins transmitting one or more advertisement data packets in the second advertising mode 204 that include the unique session identifier, the implantable device can be configured to ignore any incoming data packets from devices other than those from the specific external clinician device. For example, the implantable device can receive incoming connection requests (e.g., for a clinician session or for another type of telemetry communication session) from various devices employing the first telemetry communication protocol that received an advertisement data packet transmitted by the implantable device. However, while in the second advertising mode 204, the implantable device can examine received external clinician connection requests to determine whether the received external clinician connection requests were provided by the specific external clinician device that provided the clinician session initiation request. In an exemplary embodiment, the specific clinician session device can be configured to include, in a clinician session connection request sent to the implantable device using the first telemetry communication technology/protocol (e.g., BLE), the identifier for the specific external clinician device (e.g., the external clinician device RFM address, the external clinician device MAC address or the like) that was provided to the implantable device by the external clinician device with the clinician session ignition request. According to this embodiment, the implantable device can determine whether a received clinician session connection request was provided by the specific external clinician device based on recognition of the identifier for the specific external clinician device in the clinician session connection request. Based on a determination that a received clinician session connection request was provided by the specific external clinician device, the implantable device can establish a clinician session with the specific external clinician device.

In one or more embodiments, the implantable device can restrict the duration of time after which the implantable device enters into the second advertising mode 204 for establishment of a clinician session. This duration of time is referred to herein as the "advertisement period." For example, the implantable device may not receive a clinician session connection request within the advertisement period, thereby causing the advertisement period to expire. In another example, the implantable device may not receive an external clinician connection request from the specific (authorized) external clinician device within the advertisement period, thereby causing the advertisement period to expire. In yet another example, the implantable device may receive a clinician session connection request from the specific external clinician device yet be unable to respond to the clinician session connection request or otherwise establish the clinician session with the specific external clinician device due to channel interference, low received signal strength (e.g., based on separation of the implantable device and the specific external clinician device beyond wireless transmission range), or another factor. In some implementations, the advertisement period associated with the second advertising mode 204 is set to five minutes. However, it should be appreciated that the advertisement period can include any suitable length of time that facilities establishing a clinician session with an authorized external clinician device while limiting an amount of current drain associated with fruitlessly advertising at the relatively high rate.

As identified by transition event 228, the implantable device can be configured to transition from the second advertising mode 204 to the first advertising mode based on expiration of the advertisement period and the satisfaction of sub-condition 1 (e.g., MRI mode is disabled, implantation is detected, and external monitoring is enabled). If the advertisement period expires and sub-condition 1 is not satisfied, then the implantable device can be configured to transition from the second advertising mode 204 to the disabled mode (not shown in state diagram 200). Transition event 222 further indicates another transition event that can cause the implantable device to transition from the second advertising mode 204 to the disabled mode 201, the start of a protocol-2 telemetry session. As indicated by transition event 212, the implantable device can also be configured to transition to the disabled mode 201 from the first advertising mode 203 if a protocol-2 telemetry session is started between the implantable device and an external device while the implantable device is operating in the first advertising mode 203 or the implantable device detects a defined context of the implantable device that indicates RF telemetry communication is unnecessary, undesirable or unsafe for use by the implantable device (e.g., no detection of implantation of the implantable device into a body, enablement of MRI mode or disablement of a remote monitoring functionality of the implantable device).

Other transition events (not shown) that can trigger the implantable device to transition from the slow advertising mode 203 to the disabled mode can include events associated with battery consumption of the implantable device. For example, the implantable device can be configured to monitor the power level of the implantable device and transition from the first advertising mode 203 to the disabled mode 201 if the power level of the implantable device falls below a threshold level. In another example, while operating in the first advertising mode, the implantable device can be configured to monitor an amount of unauthorized or unsuccessful requests to establish a telemetry session with the implantable device over a defined period of time (e.g., a calendar day). The implantable device can further transition from the first advertising mode 203 to the disabled mode based on the amount of unauthorized or unsuccessful requests exceeds a threshold amount. In yet another example, while operating in the first advertising mode 203, the implantable device can be configured to monitor an amount of telemetry usage (e.g., in duration of time or bytes) of the implantable device over a defined period of time (e.g., a calendar day) and transition to the disabled mode 201 if the amount of telemetry usage exceeds an allotted amount for the defined period of time.

With reference to clinician session mode 206, while operating in the clinician session mode 206, the implantable device can be configured to perform or conduct a clinician session in accordance with one or more parameters defined for the clinician session. For example, the parameters can define what type of data the respective devices are authorized to communicate with one another and how the data should be formatted. The parameters can also define how the devices are to communicate different types of data with one another (e.g., using one-way communications or two-way communications, duration between communication signals, number of data packets transmitted, receiver and transmitter activation and deactivation periods, etc.), and when the devices are to communicate different types data with one another. The parameters can also define when and how to encrypt and decrypt data communicated via the clinician session. In various embodiments, one or more parameters of a clinician session are defined and stored in memories of the respective devices. For example, the implantable device can be preprogrammed to with information defining general communication parameters and protocols to employ during a clinician session. In another embodiment, one or more communication parameters and protocols for a clinician session can be established and agreed upon between the implantable device and the external clinician device at the time of establishment of the clinician session.

The type of data communication performed between the implantable device and the external clinician device during a clinician session will vary depending on the features and functionalities of the implantable device and the purpose of the clinician session. The implantable device and the external clinician device are configured to encrypt and decrypt data communicated during the clinician session using the one or more session keys generated by the implantable device in response to reception of the clinician session request from the external clinician device (e.g., transition event 210 and transition event 224). In various embodiments, a clinician session can facilitate dynamic bi-directional (e.g., one-way and two-way) communication between the implantable device and the external clinician device. Thus in various embodiments, while in clinician session mode 206, the implantable device maintains receiver activation to facilitate efficient bi-directional communication. For example, as indicated by transition event 244, during clinician session mode 206, the implantable device can receive one or more downlink data packets from the external clinician device (e.g., data packets including commands or programming information, etc.), and process uplink data packets for transmission to the external clinician device (e.g., data packets including waveform information). In some implementations, during a clinician session, the external clinician device can request and receive physiological data monitored by the implantable device in real time or non-real time. For example, transition event 240 indicates that during the clinician session mode 206, the implantable device can enable or disable a live waveform mode. In particular, in an embodiment in which the implantable device is an ICD, the ICD can be configured to capture electrical signals of the heart via one or more leads (e.g., leads 110a,b), referred to herein as waveform data. The live waveform mode refers to an operating mode of the implantable device wherein the implantable device can transmit waveform data to the external clinician device in real-time (e.g., as it is captured) while the patient is interacting with the clinician operating the external clinician device. The enablement and disablement of the live waveform mode can be responsive to a defined event (e.g., establishing the clinician session) and/or response to commands received from the external clinician device. In another example, during an external clinician device, the external clinician device may program or reconfigure one or more operating parameters of the implantable device via the transmission of command line scripts to the implantable device.

The implantable device can be configured to transition out of clinician session mode 206 and into the first advertising mode 203, the second advertising mode 204, disabled mode 201, or standby mode 205. As identified by transition event 232, the implantable device can be configured to transition from the clinician session mode 206 to the first advertising mode 203 in response to closing of the clinician session and the satisfaction of sub-condition 1 (i.e., MRI mode is disabled, implantation is detected, and external monitoring is enabled). If the clinician session is closed and sub-condition 1 is not satisfied, then the implantable device can transition from the clinician session mode 206 to the disabled mode (not shown in state diagram 200). In some embodiments, if the external session is closed and the implantable device enters the first advertising mode, the implantable device enables telemetry communication by the implantable device using the second telemetry communication technology/protocol. In addition, if the clinician session is closed, the implantable device can clear the authorization information established for the clinician session by the implantable device in response to reception of the clinician session initiation request (e.g., transition event 210 and transition event 224). In particular, the implantable device can clear, or remove the authorization from memory of the implantable device or otherwise render the authorization information unusable. For example, the implantable device can clear the unique session identifier, the unique session key or keys and the identifier for the specific external clinician device. As a result, a new clinician session cannot be established between the implantable device and the specific external clinician device using the authorization information. In order for a new clinician session to be established between the implantable device and the specific external clinician device, in this embodiment, the external clinician device must send the implantable device a new clinician session initiation request and the implantable device must generate new authorization information.

As identified by transition event 230, the implantable device can transition from the clinician session mode 206 to the second advertising mode 204 in response to loss of the clinician session and the satisfaction of sub-condition 2. Sub-condition 2 includes the disablement of MRI mode. If the clinician session is lost and sub-condition 2 is not satisfied (e.g., MRI mode is enabled), then the implantable device can transition from the clinician session mode 206 to the disabled mode (not shown in state diagram 200). Loss of a clinician session refers to a loss in the integrity of the telemetry connection between the implantable device and the clinician session device in association with the clinician session. For example, loss of a clinician session can include an inability to receive or transmit data packets by the implantable device and/or the external clinician device in association with the clinician session, or an inability to receive or transmit data packets by the implantable device and/or the external clinician device with a defined level of throughput. Loss of a clinician session can be caused by various factors such as, but not limited to, channel interference, separation of the implantable device and the specific external clinician device beyond wireless transmission range, or another factor. In some embodiments, if the external session is lost and the implantable device enters the second advertising mode 204, the implantable device can enable telemetry communication using the second telemetry communication technology/protocol (e.g., induction). In addition, the advertisement period can be reset (e.g., to five minutes). The implantable device and the specific external clinician device can then be provided the duration of the advertisement period to reconnect and re-establish the clinician session using the authorization information. In one or more embodiments, if the implantable device was employing the waveform mode during the clinician session when the clinician session was lost and subsequently re-establishes the clinician session with the external clinician device, the implantable device can be configured to automatically enable or activate the waveform mode upon reestablishment of clinician session.

The standby mode 205 is an energy conservation mode in which the implantable device uses less power relative to the power to operate in the clinician session mode 206 while maintaining establishment of the clinician session with the external clinician device. The standby mode 205 can facilitate reducing power consumption associated with performance of the external clinician telemetry session by the implantable device, for example during periods of reduced or paused telemetry communication activity between the implantable device and the external clinician device. For example, the implantable device can enter standby mode 205 in response to a request received from the external clinician device to enter standby mode (e.g., at a time when the clinician is not examining live waveform data, is not programming the implantable device, when the patient leaves to use the restroom, etc.). The implantable device can also enter the standby mode 205 in response to detection of a defined period (e.g., 2 minutes, 5 minutes, 15 minutes, etc.) of telemetry communication inactivity. In one or more embodiments, the implantable device can be configured to interpret either of these transition events as a start standby signal. The implantable device can be configured to begin operating in standby mode 205 based on reception of a start standby signal, as indicated by transition event 236. In one or more embodiments, if the implantable device was employing waveform mode when operating in the clinician session mode 206, the implantable device can disable waveform mode when entering the standby mode 205.

During the standby mode 205, the implantable device can maintain and perform the clinician session with a reduced functionality relative to the functionality employed during the clinician session mode 206. For example, while operating in clinician session mode 206, the implantable device can be either actively transmitting one or more data packets with actionable data, such as waveform data or other types of data requested by the clinician device from the implantable device, or receiving one or more data packets including actionable data (e.g., programming information). While in standby mode 205, this active data communication is not being conducted between the implantable device and the external clinician device. For example, while in standby mode 205, the implantable device can maintain establishment of the clinician session with the external clinician device yet either does not communicate data with the external clinician device or communicates a limited amount of idle data to maintain the clinician session. In some embodiments, while in standby mode 205, the implantable device can transmit one or more data packets including idle or non-actionable information. As used herein, the term "actionable data" refers to information that is capable of being acted upon. For example, actionable data can include a command (e.g., a programming command, a command to exit or enter standby mode, an acknowledgment signal, etc.), or informative information associated with operation of the implantable device. Actionable data can vary. On the contrary, idle data refers to data that solely servers as a heartbeat or indication that the implantable device is maintaining a connection with the clinician device. The implantable device can transmit one or more idle data packets according to a low duty cycle (e.g., once every 10 seconds, once every 30 seconds, once every minute, etc.) and deactivate its transmitter and/or receiver in between transmission of the respective idle packets. In other embodiments, during the standby mode 205, the implantable device can deactivate the RF transmitter and activate the RF receiver according to a low duty cycle, (e.g., once every ten seconds) to receive a wake up signal that causes the implantable device to transition back to clinician session mode 206.

In some implantations, rather than employing standby mode 205, the implantable device is configured to remain in the clinician session mode 206 yet modify an aspect of data transmission and/or reception by the implantable device to facilitate reducing power consumption by the implantable device. For example, the implantable device can remain in the clinician session mode 206 and prevent transmission of real-time waveform data to the external clinician device while enabling rapid bi-directional communication between the implantable device and the external clinician device. In another example, the implantable device can remain in the clinician session mode 206 and provide real-time one-way data transmissions to the external clinician device (e.g., waveform data) yet deactivate the RF receiver of the implantable device for prolonged periods of time to reduce battery draw by the implantable device when reception of data communications from the external clinician device is not expected.

Once in standby mode 205, the implantable device can transition back to the clinician session mode 206, the first advertising mode 203, the second advertising mode 204, or the disabled mode 201. In one or more embodiments, the implantable device can transition from the standby mode 205 back to the clinician session mode 206 in response to reception of a stop standby signal (e.g., a wake up signal) transmitted by the external clinician device, or in response to reception of downlink information, as indicated by transition event 238. In one or more embodiments, to enter standby mode, the external clinician device can transmit a signal over the communication link instructing the implantable device the turn off waveforms and enter a low power state, or standby mode 205. The circuitry, components and/or devices that can cause the implantable device to transition to standby mode can be provided in the external clinician device in some embodiments. In other embodiments, circuitry, components and/or devices that can cause the implantable device to transition to standby mode can be provided in the implantable device. All such embodiment are envisaged.

In one or more embodiments, if the implantable device was employing the waveform mode during the clinician session mode 206 before entering standby mode 205, the implantable device can be configured to enable or activate the waveform mode upon transitioning from the standby mode 205 back to the clinician session mode 206.

In one or more additional embodiments, the external clinician device is configured to manage entry and exit of the implantable device to and from the standby mode 205. For example, while operating in the clinician session mode 206, the external clinician device can send the implantable device a command to enter standby mode. The implantable device can further be configured to enter standby mode only in response to reception of this command from the external clinician device during an established clinician session with the external clinician device. Likewise, while operating in the standby mode 205, the external clinician device can send the implantable device a command to exit standby mode. The implantable device can further be configured to exit standby mode only in response to reception of this exit standby mode command.

The implantable device can be configured to transition from standby mode 205 to the first advertising mode 203 in response to closing of the clinician session and the satisfaction of sub-condition 1 (i.e., MRI mode is disabled, implantation is detected, and external monitoring is enabled), as identified in by transition event 226. If the clinician session is closed and sub-condition 1 is not satisfied, then the implantable device can transition to the disabled mode (not shown in state diagram 200). As described above with reference to transition event 232, in some embodiments, if the external session is closed and the implantable device enters the first advertising mode, the implantable device enables telemetry communication by the implantable device using the second telemetry communication technology/protocol. In addition, if the clinician session is closed, the implantable device can also be configured to clear the authorization information established for the clinician session by the implantable device in response to reception of the clinician session initiation request (e.g., transition event 210 and transition event 224).

As identified by transition event 242, the implantable device can be configured to transition from the standby mode 205 to the second advertising mode 204 in response to loss of the clinician session and the satisfaction of sub-condition 2 (i.e., the disablement of MRI mode). If the clinician session is lost and sub-condition 2 is not satisfied (e.g., MRI mode is enabled), then the implantable device can transition from the standby mode 205 to the disabled mode (not shown in state diagram 200). As described above with reference to transition event 230, in some embodiments, if the external session is lost and the implantable device enters the second advertising mode 204, the implantable device can enable telemetry communication by the implantable device using the second telemetry communication technology/protocol (e.g., induction). In addition, the advertisement period can be reset (e.g., to five minutes). The implantable device and the specific external clinician device can then have the duration of the advertisement period to reconnect and re-establish the clinician session using the authorization information.

With reference back to the first advertising mode 203. The implantable device can transition from the first advertising mode 203 to the monitoring session mode 202 in response to establishment of a monitoring session with an authorized external monitoring device, as identified by transition block 220. During the monitoring session mode 202, the implantable device and an authorized external monitoring device conduct or perform a monitoring session. For example, the implantable device can transmit monitored information to the external monitoring device including, but not limited to, physiological information captured by the implantable device about the patient or monitored operating parameters associated with performance of the implantable device. In various embodiments, the type of information the implantable device can communicate with the external monitoring device during a monitoring session can be defined and programmed into the implantable device. In one or more embodiments, the implantable device can be also programmed with information identifying one or more external monitoring devices with which the implantable device is authorized to establish a monitoring session. For example, prior to implantation or after implantation, (e.g., during a clinician session, or a protocol-2 telemetry session), the implantable device can receive and store information identifying the one or more external monitoring devices with which the implantable device is authorized to establish a monitoring session. The one or more devices, for example, can include a home monitoring device provided to the patient in association with receiving the implantable device or a smartphone or tablet device previously owned and/or operated by the patient and later programmed to facilitate a remote monitoring functionality associated with the patient's implanted device. In one or more implantations, these authorized external devices can receive the authorization information (e.g., secret keys, unique identifiers, etc.) for establishment of a trusted relationship with the implantable device from a trusted server device or system associated with managing and ensuring telemetry security of various patients' implanted devices. In various embodiments, the one or more external monitoring devices that are authorized to establish a monitoring session can be paired with the implantable device.

During the first advertising mode 203, the implantable device can transmit one or more advertisement data packets according to a defined RF telemetry communication protocol (e.g., BLE). As noted above, in various embodiments, the transmission rate is lower or slower than the transmission rate employed by the implantable device to transmit one or more advertisement data packets during the second advertising mode 204. For example, the transmission rate during the first advertising mode 203 may be about one advertisement data packet every three minutes compared to one advertisement data packet every one second for the second advertising mode 204. The one or more advertisement data packets transmitted by the implantable device during the first advertising mode can include information indicating the implantable device is ready and available to conduct a monitoring session. In one or more embodiments, the implantable device can be configured to receive a response to a transmitted advertisement data packet that was received by an external device. For example, the response can include a request to establish a telemetry session with the implantable device. The implantable device can be configured to then determine whether the response was provided by an external monitoring device with which the implantable device is authorized to establish a monitoring session. In response to a determination that the device is unauthorized, the implantable device can continue to remain in the first advertising mode. If however the implantable device can determine the external device is an authorized external monitoring device, the implantable device can establish a monitoring session with the authorized external monitoring device and transition into the monitoring session mode 202.

The implantable device can be configured to transition from the monitoring session mode 202 to the first advertising mode 203 in response to the transition events identified by transition event 216. In one implementation, the implantable device can be configured to transition from the monitoring session mode 202 to the first advertising mode 203 based on closing of the monitoring session and satisfaction of sub-condition 1 (i.e., MRI mode is disabled, implantation is detected, and external monitoring is enabled). If the monitoring session is closed and sub-condition 1 is not satisfied, the implantable device can be configured to transition from the monitoring session mode 202 to the disabled mode 201. The implantable device can also be configured to transition from the monitoring session mode 202 to the first advertising mode 203 in response to loss of the monitoring session. The implantable device can also be configured to transition to the disabled mode 201 based on reception of a request to establish a protocol-2 telemetry session with an external device while operating in the monitoring session mode 202, as identified by transition event 221.

Referring again to FIGS. 1 and 2, system 100 provides several technical solutions to technical drawbacks associated with existing implantable device telemetry systems. In particular, implantable devices (e.g., implantable device 104), including IMDs, are increasing in complexity while shrinking in size. One hurdle to achieving such small and highly functional devices is efficient power management. Many implantable devices, such as implantable device 104, operate from power sources that have a limited lifespan and/or are not rechargeable. As such, after the implantable device is implanted within the human body and the lifespan of the power source has been reached, the implantable device may need to be removed and replaced. Telemetry communication performed between an implantable device and an external device can have a significant impact on the lifespan of the power source of an implantable device.

System 100 facilitates enhanced battery conservation associated with telemetry operations of the implantable device 104 by employing different communication modes of operation that are respectively associated with different amounts of battery drain, including but not limited to: disabled mode 201, monitoring session mode 202, first advertising mode 203, second advertising mode 204, standby mode 205 and clinician session mode 206. The different amounts of battery draw associated with these different communication modes are attributed to activation of different types of telemetry hardware circuitry components of the implantable device (e.g., RF components and induction components), and different amounts of activation of the respective telemetry hardware circuitry components (e.g., different duty cycles for receiver and transmitter activation). Because activation and deactivation of different telemetry hardware circuitry components involves physical and electrical processes and components, a human is unable to replicate or perform the subject battery conservation techniques.

In addition, the subject battery conservation techniques provide substantial improvements in the field of implantable device telemetry operations. In accordance with system 100, the activation of different types of telemetry communication hardware components and the different amounts of activation of the respective telemetry communication hardware components are selected and optimized to balance the type of telemetry communication needed by the implantable device 104 at any given time over the lifetime of the implantable device 104, and the degree of communicative responsiveness needed for the implantable device 104 in association with the type of telemetry communication session performed (e.g., a protocol-2 telemetry session, a monitoring session, a clinician session, etc.). For example, when RF telemetry communication is not needed or unsafe, the implantable device 104 can operate using the disabled mode 201, thereby minimizing power consumption associated with activation of the one or more RF components of the implantable device. In addition, when the implantable device 104 is not actively receiving downlinks or providing uplinks during a clinician session, the implantable device 104 can operate using the standby mode 205, thereby minimizing power consumption associated with activation of the one or more RF components. The implantable device 104 can also employ first and second advertising modes which are associated with different amounts of RF transmitter and receiver activation that has been optimized based on the degree of communicative responsiveness needed for the implantable device in association with establishing and re-establishing a monitoring session verses a clinician session. For example, in one or more implementations, during the first advertising mode 203, the implantable device 104 can activate its RF transmitter once every N minutes (e.g., three minutes) to transmit an advertisement data packet and activate its receiver for M seconds (e.g., five seconds) thereafter to enable reception of a response. On the other hand, during the second advertising mode 204, the implantable device 104 can activate its RF transmitter once every X seconds (e.g., sixty seconds) to transmit an advertisement data packet and maintain receiver activation between advertisement data packets to enable reception of a response. In one or more implementations, X can be at least 100% greater than N, and, in some embodiments, at least 200% greater than N, and in some embodiments, 300% greater than N.

In various embodiments, the implantable device 104 can also be configured to detect transition events and cause the implantable device to transition into and out of the different communication modes of operation, each of which respectively involve a physical process or reaction by the implantable device 104 that cannot be performed by a human. In particular, movement into and out of the respective communication modes involves activation and/or deactivation, by the implantable device 104, of one or more telemetry communication hardware components of the implantable device104. In addition, the ability to detect the various transition events and conditions is rooted in a physical mechanism that involves hardware circuitry of the implantable device 104. For example, in some implementations, the implantable device 104 can be configured to detect implantation based on electrical signals received from connected leads (e.g., leads 110*a,b*). In another example, the implantable device 104 can be configured to detect when to transition to the second advertising mode based on reception of an induction signal via activation of an induction antenna of the implantable device 104. In another example, the implantable device 104 can configured to determine when to transition to the monitoring session mode 202 or the clinician session mode 206 based on reception, via an RF receiver or transceiver of the implantable device, of a defined response signal within a defined advertisement period of time.

System 100 further can provide substantial improvements in the field of implantable medical device telemetry security. In particular, system 100 facilitates enhanced security associated with establishing and performing a telemetry session with the implantable device 104 using an RF-based telemetry communication technology/protocol (e.g., BLE) that enables rapid (and high power consuming) bi-directional telemetry communication with the implantable device 104 of data considered highly invasive or sensitive (e.g., programming data or waveform data associated with a clinician session). Modern IMDs (e.g., implantable device 104) are entrusted with vital tasks such as measuring and collecting data about vital signs and facilitating the provisioning of the collected data to doctors and nurses using telemetry communication. For example, in many applications, vital information is periodically and automatically communicated between an implantable device and an external device, such as an external device accessible to the patient implanted with the implantable device and/or medical caregiver.

The technical security mechanism employed by the implantable device 104 in association with system 100 can employ an authorized external clinician device (e.g., external clinician device 120) to generate and send a clinician session initiation request (e.g., transition event 210 or transition event 224) using a non-RF-based telemetry communication protocol/technology (e.g., induction) to cause the implantable device 104 to transition into a dedicated communication mode (e.g., the second advertising mode 204) via which the implantable device 104 can establish a clinician session. Based on reception of the clinician session request (e.g., via activation of non-RF-based telemetry hardware components of the implantable device 104), the implantable device can interpret the clinician session request and generate unique authorization information that can be employed for establishment and performance of the currently requested clinician session. In particular, in one embodiment, the unique authorization information restricts establishment of the currently requested clinician session with the implantable device 104 to only the authorized external clinician device that provided the non-RF-based session initiation signal. The unique authorization information can further restrict usage of the authorization information for only the establishment of the currently requested session. As a result, in one embodiment, if the clinician session cannot be established (e.g., due to expiration of the advertisement period, transition event 224) or is closed, the authorization information becomes void and cannot be employed to conduct a new clinician session with the implantable device 104.

Figure 3:
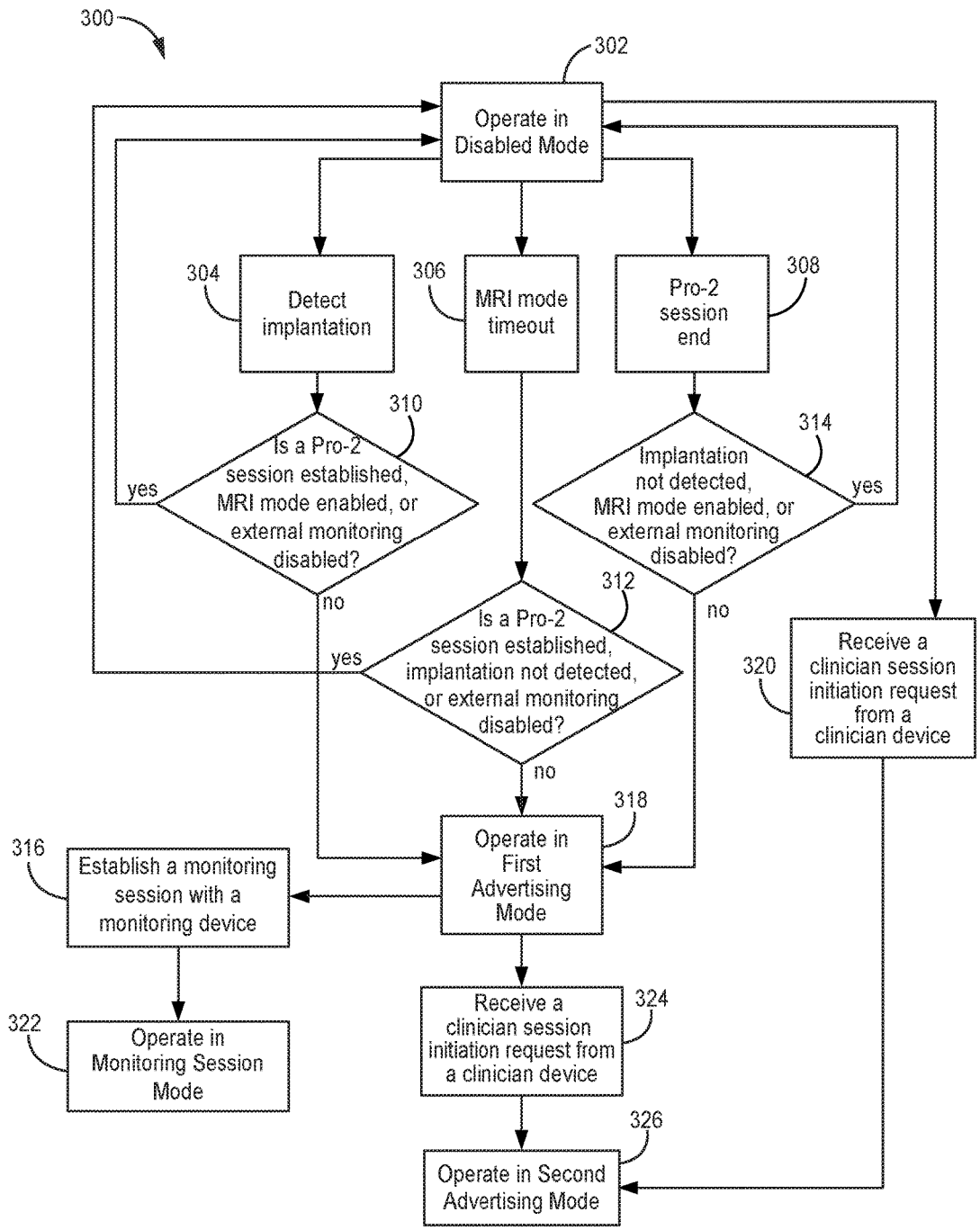
FIG. 3 illustrates an example, non-limiting flow diagram of a method facilitating managing operation of an implantable device in a disabled mode, a first advertising mode, a second advertising mode, and a monitoring session mode in accordance with one or more embodiments described herein.

Referring now to FIG. 3, illustrated is an example, non-limiting flow diagram of a method 300 facilitating managing operation of an implantable device (e.g., implantable device 104) in a disabled mode, a first advertising mode, a second advertising mode, and a monitoring session mode in accordance with one or more embodiments described herein. Repetitive description of like elements employed in respective embodiments described herein is omitted for sake of brevity.

Method 300 is initially described with reference to 302 wherein the implantable device can operate in the disabled mode. At 304, the implantable device detects that the implantable device has been implanted into the body. Based on detecting implantation, the implantable device then can determine at 310 whether a protocol-2 telemetry session is established between the implantable device and an external device, whether MRI is enabled, or whether external monitoring is disabled. In response to a decision at 310 that a protocol-2 telemetry session is established between the implantable device and an external device, MRI is enabled, or external monitoring is disabled, method 300 returns to the implantable device operating in the disabled mode at 302. However, in response to a decision at 310 that a protocol-2 telemetry session is not established between the implantable device and an external device, MRI is disabled, and external monitoring is disabled, the implantable device can operate in the first advertising mode at 318. At 306, the implantable device detects that the MRI mode of the implantable device has timed-out. Based on detecting the MRI mode timeout, the implantable device then can determine at 312 whether a protocol-2 telemetry session is established between the implantable device and an external device, whether implant detection is false, or whether external monitoring is disabled. In response to a decision at 312 that a protocol-2 telemetry session is established between the implantable device and an external device, implant detection is false, or external monitoring is disabled, method 300 can return to the implantable device operating in the disabled mode at 302. However, in response to a decision at 312 that a protocol-2 telemetry session is not established between the implantable device and an external device, implant detection is true, and external monitoring is disabled, the implantable device can operate in the first advertising mode at 318. At 308, the implantable device can detect that an established protocol-2 telemetry session has ended. Based on detecting the close of the protocol-2 telemetry session, the implantable device then can determine at 314 whether implant detection is false, whether MRI is enabled, or whether external monitoring is disabled. In response to a decision at 314 that implant detection is false, MRI is enabled, or external monitoring is disabled, method 300 can return to the implantable device operating in the disabled mode at 302. However, in response to a decision at 314 that implant detection is true, MRI is disabled, and external monitoring is disabled, the implantable device can operate in the first advertising mode at 318.

While operating in the first advertising mode at 318, in some implementations, at 316 the implantable device can establish a monitoring session with an external monitoring device (e.g., external monitoring device 116). The implantable device then begins operating in the monitoring session mode at 322. In another implementation, while operating in the first advertising mode at 318, the implantable device can receive a clinician session initiation request from a clinician device at 324. Based on reception of the clinician session initiation request, the implantable device can transition to operating in the second advertising mode at 326. In yet another implementation, while operating in the disabled mode at 302, the implantable device can receive a clinician session initiation request at 320, and based on reception of the clinician session initiation request, the implantable device can transition to operating in the second advertising mode at 326.

Figure 4:
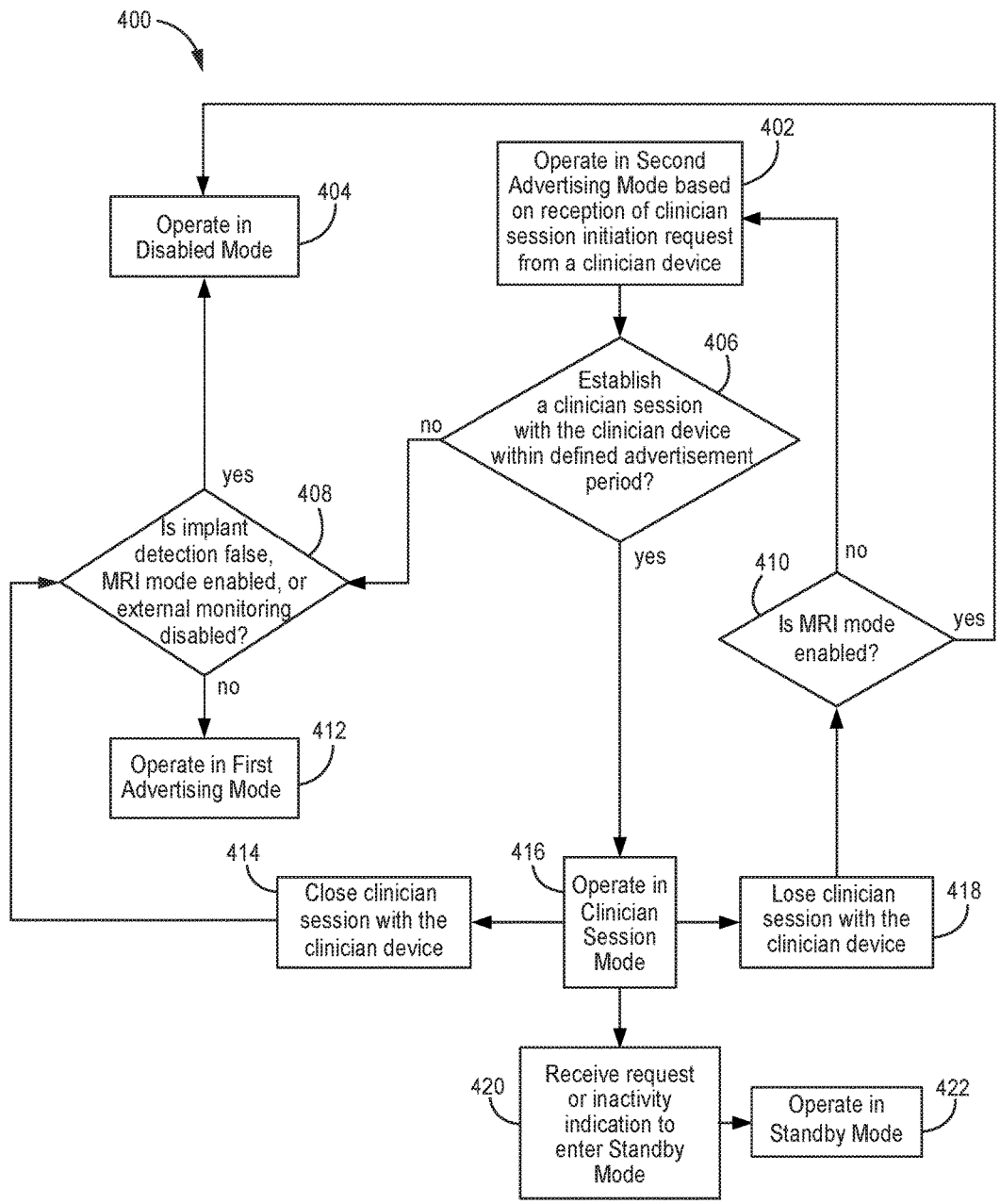
FIG. 4 illustrates an example, non-limiting flow diagram of a method facilitating managing operation of an implantable device in a disabled mode, a first advertising mode, a second advertising mode, a clinician mode and a standby mode in accordance with one or more embodiments described herein.

FIG. 4 illustrates an example, non-limiting flow diagram of a method 400 facilitating managing operation of an implantable device (e.g., implantable device 104) in a disabled mode, a first advertising mode, a second advertising mode, clinician mode and a standby mode in accordance with one or more embodiments described herein. Repetitive description of like elements employed in respective embodiments described herein is omitted for sake of brevity.

Method 400 is initially described with reference to 402 wherein the implantable device can operate in the second advertising mode based on reception of a clinician session initiation request from a clinician device. At 406, the implantable device can determine whether it has established a clinician session with the clinician device within the defined advertisement period (e.g., five minutes). If so, the implantable device can then transition to operating in the clinician session mode at 416. If not, the implantable device then can determine, at 408, whether implantation is not detected, whether MRI is enabled, or whether external monitoring is disabled. In response to a determination that implantation is not detected, MRI is enabled, or external monitoring is disabled, the implantable device can transition to operating in the disabled mode at 404. However, in response to a determination that implantation is detected, MRI is disabled, and external monitoring is enabled, the implantable device can transition to operating in the first advertising mode at 412.

With reference to 416, in one implementation, while operating in the clinician session mode, at 414 the clinician session established between the implantable device and the clinician device is closed. With this implementation, the implantable device then can determine at 408 whether implantation is not detected, whether MRI is enabled, or whether external monitoring is disabled. In response to a determination that implantation is not detected, MRI is enabled, or external monitoring is disabled, the implantable device can transition to operating in the disabled mode at 404. However, in response to a determination that implantation is detected, MRI is disabled, and external monitoring is enabled, the implantable device can transition to operating in the first advertising mode at 412.

With reference to 416, in another implementation, while operating in the clinician session mode, at 418, the clinician session established between the implantable device and the external clinician device may be lost. The implantable device then can determine at 410 whether MRI is enabled. If MRI is enabled, the implantable device begins operating in the disabled mode at 404. However, if MRI is disabled, the implantable device returns to operating in the second advertising mode at 402. In yet another implementation, while operating in the clinician session mode at 416, the implantable device can receive a request or inactivity indication to enter standby mode. For example, the external clinician device can send the implantable device a request to enter standby mode to allow the patient implanted with the implantable device to use the restroom. In another example, the external clinician device can disable a waveform mode of the implantable device and not transmit or receive data packets to or from the implantable device for a defined inactivity period (e.g., fifteen minutes). As a result, the implantable device can enter standby mode at 422.

Figure 5:
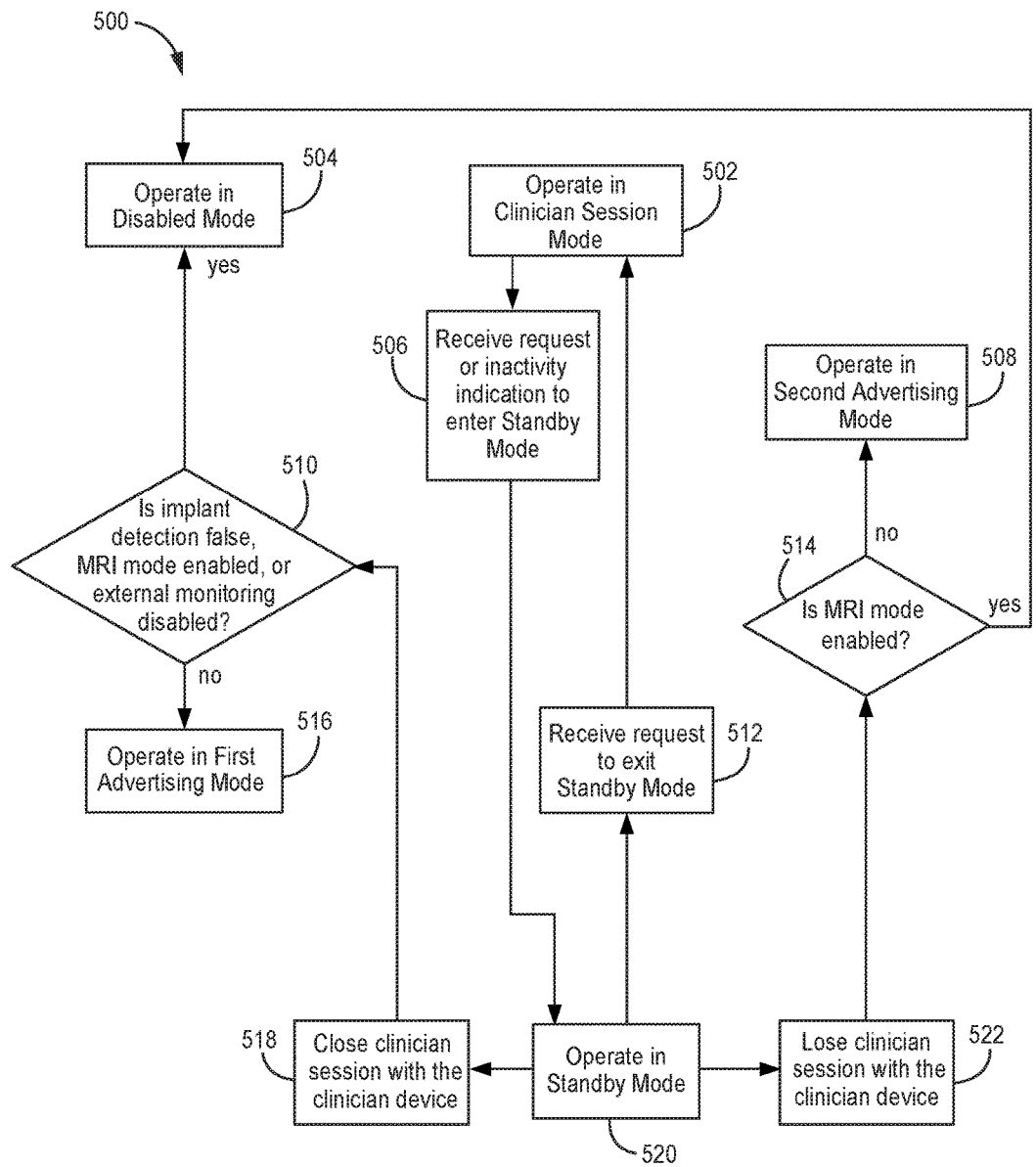
FIG. 5 illustrates another example, non-limiting flow diagram of a method facilitating managing operation of an implantable device in a disabled mode, a first advertising mode, a second advertising mode, a clinician mode and a standby mode in accordance with one or more embodiments described herein.

FIG. 5 illustrates another example, non-limiting flow diagram of a method 500 facilitating managing operation of an implantable device (e.g., implantable device 104) in a disabled mode, a first advertising mode, a second advertising mode, clinician mode and a standby mode in accordance with one or more embodiments described herein. Repetitive description of like elements employed in respective embodiments described herein is omitted for sake of brevity.

Method 500 is initially described with reference to 502 wherein the implantable device can operate in the clinician session mode. At 506, the implantable device can receive a request or inactivity indication to enter standby mode (e.g., from clinician device 120). In response to the request, the implantable device can then enter standby mode at 520. After the implantable device begins operating in standby mode, in one implementation, at 512, the implantable device can receive a request to exit standby mode. In response to the request to exit standby mode, the implantable device can then re-enter the clinician session mode at 502. In another implementation, after the implantable device is operating in standby mode, at 518, the clinician session established between the implantable device and the clinician device is closed. With this implementation, the implantable device can determine at 510 whether implantation is not detected, whether MRI is enabled, or whether external monitoring is disabled. In response to a determination that implant detection is false, MRI is enabled, or external monitoring is disabled, the implantable device can transition to operating in the disabled mode at 504. However, in response to a determination that implantation is detected, MRI is disabled, and external monitoring is enabled, the implantable device can transition to operating in the first advertising mode at 516. With reference to 522, in yet another implementation, while operating in the standby mode, at 522, the clinician session established between the implantable device and the external clinician device is lost. The implantable device can then can determine at 514 whether MRI is enabled. If MRI is enabled, the implantable device can begin operating in the disabled mode at 504. However, if MRI is disabled, the implantable device can return to operating in the second advertising mode at 508.

Figure 6:
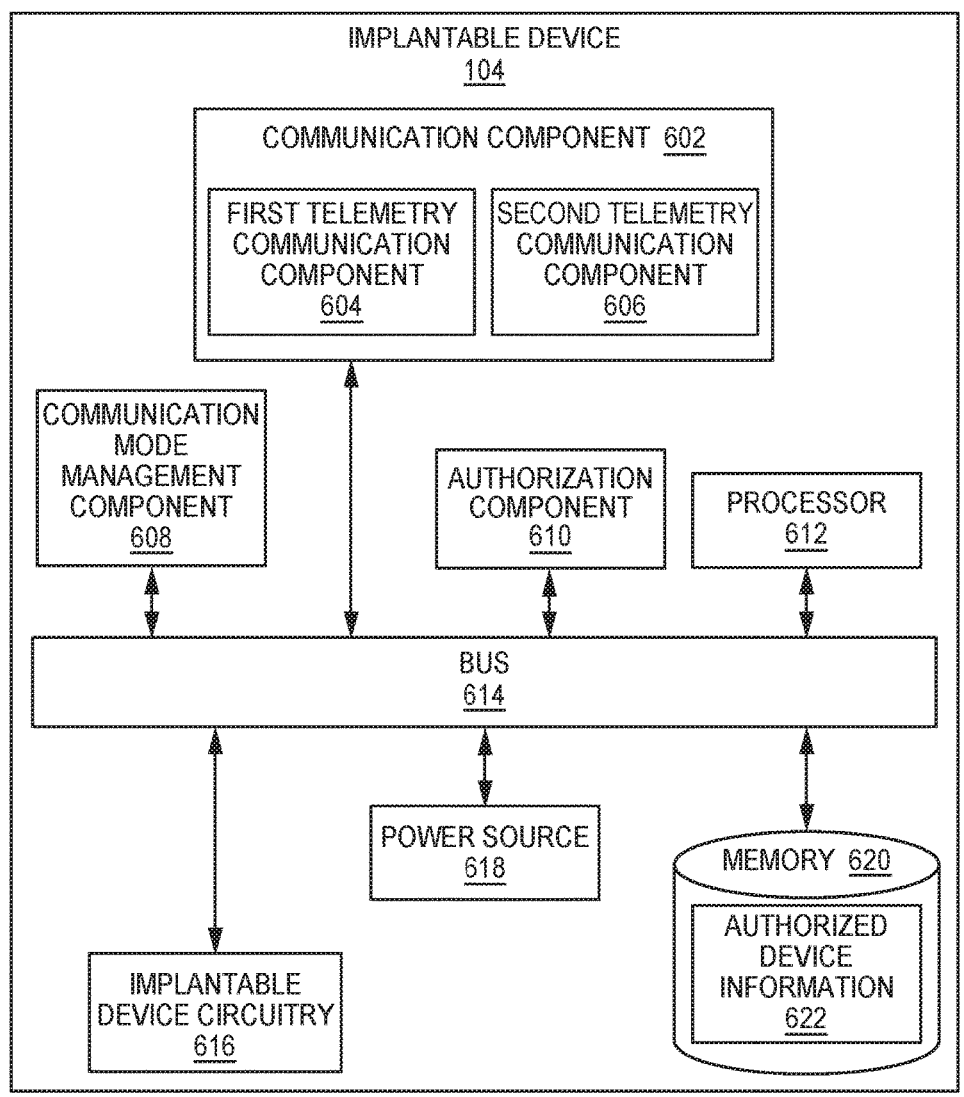
FIG. 6 illustrates a block diagram of an example, non-limiting implantable device in accordance with one or more embodiments described herein.

FIG. 6 illustrates a block diagram of an example, non-limiting implantable device (e.g., implantable device 104) in accordance with one or more embodiments described herein. The implantable device 104 includes communication component 602, communication mode management component 608, and authorization component 610. Implantable device 104 also includes implantable device circuitry 616 and power source 618. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

Implantable device 104 can include memory 620 configured to store computer executable components and instructions. Implantable device 104 can also include a processor 612 to facilitate operation of the instructions (e.g., computer executable components and instructions) by the implantable device 104. Implantable device 104 can include a bus 614 that couples the various components of the implantable device 104, including, but not limited to, the communication component 602, the communication mode management component 608, the authorization component 610, the processor 612, the implantable device circuitry 616, the power source 618 and the memory 620. Repetitive description of like elements employed in other embodiments described herein is omitted for sake of brevity.

With reference to FIGS. 1, 2, and 6, the communication component 602 can be configured to facilitate telemetry communication between implantable device 104 and one or more external devices (e.g., external monitoring device 116 and external clinician device 120) using at least a first RF-based telemetry communication technology/protocol and a second telemetry communication technology/protocol. In one or more embodiments, communication component 602 includes a first telemetry communication component 604 configured to facilitate telemetry communication between the implantable device 104 and the one or more external devices according to the first RF-based telemetry communication technology/protocol. In an exemplary embodiment, the first telemetry communication technology/protocol includes BLE. For example, the first telemetry communication component 604 can control operation of an RF transceiver (or an RF transmitter-receiver) and repeater to establish an RF-based external monitoring telemetry session with external monitoring device 116 and control transmission and reception of one or more data packets by the implantable device 104 in association with the monitoring session. In another example, the first telemetry communication component 604 can control operation of an RF transceiver (or an RF transmitter-receiver) and repeater to establish an RF-based external clinician telemetry session with external clinician device 120 and control transmission and reception of one or more data packets by the implantable device 104 in association with the clinician session. In some embodiments, as an alternative or in addition to including a transceiver, the implantable device 104 can include a transmitter and a receiver that do not share common circuitry.

The communication component 602 can also include a second telemetry communication component 606 configured to facilitate telemetry communication by the implantable device 104 according to the second telemetry communication protocol/technology. In one or more implementations, the second telemetry communication technology/protocol includes a non-RF-based telemetry communication technology/protocol, such as an induction-based telemetry communication technology/protocol. For example, the second telemetry communication component 606 can include an induction antenna or coil and repeater configured to generate and receive electromagnetic induction signals in association with a protocol-2 telemetry session between the implantable device and one or more external devices. In another example, the induction antenna or coil and repeater can receive an induction signal that includes a clinician session initiation request from external clinician device. The induction antenna or coil can also generate and send an electromagnetic induction signal to the external clinician device that includes a response to the clinician session initiation request. The response can include authorization information (e.g., a UUID and one or more unique session keys) for the clinician session.

Communication component 602 can facilitate telemetry communication between the implantable device 104 and an external device (e.g., external monitoring device 116 and external clinician device 120) using a variety of networks (not shown) and/or wireless communication protocols. For example, in one or more embodiments, communication component 602 can communicate with external monitoring device 116 using NFC, or another type of communication protocol over a PAN or a LAN, (e.g., a Wi-Fi network) that can provide for communication over greater distances than NFC protocol or that can accomplish one or more aspects described herein (such as increased security).

In some embodiments, communication component 602 can control transmission and reception of one or more data packets via a communication channel associated with a communication protocol utilizing lower energy consumption than a conventional communication protocol for wirelessly transmitting data. For example, in a non-limiting example, the first telemetry communication component 604 controls transmission and reception of data packets using BLE protocol. Other communication protocols that can be employed by the communication component 602 to communicate with external monitoring device 116 and/or external clinician device 120 can include, but are not limited to, other BLUETOOTH® communication protocols, a Session Initiation Protocol (SIP) based protocol, a ZIGBEE® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, an RF communication protocol, and/or other proprietary and non-proprietary communication protocols.

In one or more embodiments, communication component 602 can be configured to establish a secure or trusted telemetry session with external monitoring device 116 or the external clinician device 120 prior to facilitating the exchange of sensitive data between the implantable device 104 and the external monitoring device 116 or the external clinician device. In one implementation, in order to establish such a secure or trusted connection, after the first telemetry session, communication component 604 can receive a request from the external monitoring device 116 or the external clinician device 120 to establish a telemetry session with the implantable device 104, the implantable device 104 can determine whether the external monitoring device 116 or the external clinician device is authorized to communicate with the implantable device 104. In response to a determination that the respective devices are authorized, the first telemetry communication component 604 can proceed to establish the secure telemetry session with the respective devices using the first telemetry communication technology/protocol (e.g., BLE).

The authorization component 610 can facilitate determining whether an external device requesting to establish a telemetry session with the implantable device is authorized to do so. For example, in one or more embodiments, after the implantable device 104 can receive a monitoring session request from an external device, the authorization component 610 can determine whether the external device is an authorized external monitoring device based on authorized device information 622 stored in memory 620 including unique identification information for one or more authorized external monitoring devices with which the implantable device 104 is authorized to establish a monitoring session. For example, in association with sending a request to establish a monitoring telemetry session with the implantable device 104 after receiving an advertisement data packet transmitted by the implantable device 104 while operating in the first advertising mode 203, the external monitoring device 116 can provide the implantable device 104 with information indicating communication parameters for the telemetry session. In some embodiments, the information can also include authentication information for the external monitoring device 116 that uniquely identifies the external monitoring device 116 (e.g., a device identification number, an encrypted key, a MAC, or other suitable authentication information). This authentication information can be previously provided to the implantable device 104 and stored in the memory 620 of the implantable device as authorized device information 622. The implantable device 104 can process the received authorization information to determine whether the external monitoring device 116 is authorized to communicate with the implantable device 104.

In various additional embodiments, the authorization component 610 can be configured to generate session authorization information for a clinician session in response to reception of a clinician session initiation request by the implantable device 104 via the second telemetry communication component 606. For example, in response to reception of an induction signal including a clinician session initiation request from the external clinician device 120, the authorization component 610 can generate a unique (e.g., randomly generated) session identifier (e.g., a UUID), and one or more unique session keys. The authorization component 610 can temporarily store the session authorization information in memory 620 of the implantable device 104 along with a unique identifier (e.g., an RFM address, a MAC address or the like) for the external clinician device received from the external clinician device with the clinician session initiation request. The second telemetry communication component 606 can further generate and send a response to the external clinician device 120 including the authorization information using an induction signal. The authorization component 610 can further authorize establishment of a clinician session between the implantable device 104 and the external clinician device 120 based on reception of an RF signal based connection request, by the first telemetry communication component 604, from the external clinician device 120 including the identifier for the external clinician device. After the clinician session is established, the first telemetry communication component 604 can employ the one or more session keys to encrypt and decrypt information communicated between the implantable device 104 and the external clinician device 120.

The implantable device 104 includes communication mode management component 608 to facilitate transitioning the implantable device between the plurality of communication modes of operation, including but not limited to, the disabled mode 201, the monitoring session mode 202, the first advertising mode 203, the second advertising mode 204, the standby mode 205, and the clinician session mode 206. For example, the communication mode management component 608 can be configured to identify the occurrence of transition events (e.g., transition events 210, 212, 214, 216, 218, 220, 221, 222, 224, 226, 228, 230, 232, 234, 236, 238, 240, 242 and 244), determine whether a transition event warrants transitioning the implantable device 104 from a first communication mode to a second communication mode, and effectuate the transition accordingly. The communication mode management component 608 can employ information identifying transition events and conditions associated with the transition events (e.g., sub-condition 1 and sub-condition 2) that respectively cause the implantable device to either remain operating within a particular communication mode or transition to another communication mode.

The implantable device circuitry 616 can include hardware, software or a combination of hardware and software employed to facilitate operation of the various components of the implantable device 104. For example, the implantable device circuitry can include, but is not limited to: a pulse generator, capacitors, leads (e.g., leads 110a,b), electrodes (e.g., tip electrodes 112a,b and ring electrodes 114a,b), sensors, accelerometers, pumping mechanisms, reservoirs, communication component 602 hardware (e.g., antennas, transmitters, receivers, transceivers repeaters, etc.), a therapy output module, and the like. The implantable device circuitry 616 can facilitate various operations of the implantable device, including but not limited to, medical related operations (e.g., sensing electrical signals of the heart, dispensing a drug, etc.), and telemetry communication mode operations of the implantable device (e.g., RF telemetry and non-RF telemetry such as induction). Implantable device 104 further includes power source 618 to drive the operations of implantable device 104 and provide power to the various electrical components of the implantable device 104. In one or more embodiments, the power source includes but is not limited to, a battery, a capacitor, a charge pump, a mechanically derived power source (e.g., microelectromechanical systems (MEMs) device), or an induction component. The induction component can also be employed by the second telemetry communication component 606 to facilitate transmission and reception of inducing based telemetry signals.

Figure 7:
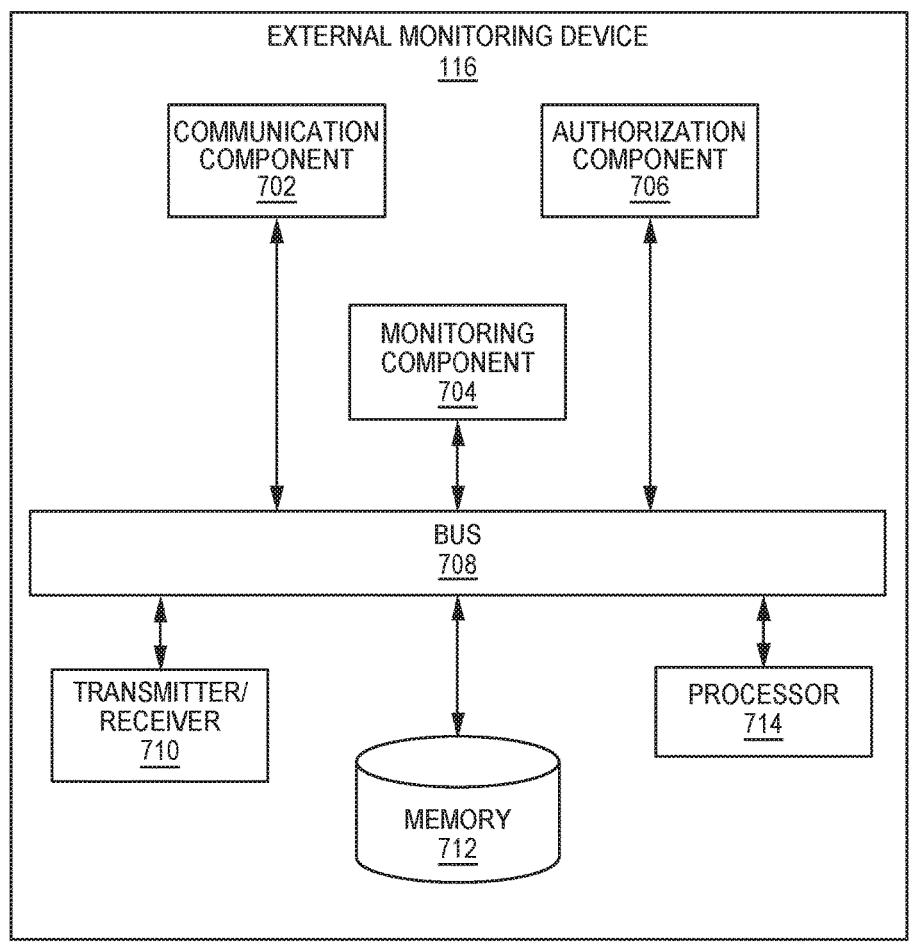
FIG. 7 illustrates a block diagram of an example, non-limiting external monitoring device in accordance with one or more embodiments described herein.

FIG. 7 illustrates a block diagram of an example, non-limiting external monitoring device (e.g., external monitoring device 116) in accordance with one or more embodiments described herein. The external monitoring device includes a communication component 702, an monitoring component 704, and an authorization component 706. The external monitoring device 116 can also include a transmitter/receiver 710. One or more of the components of external monitoring device 116 constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

The external monitoring device 116 can include memory 712 for storing the computer executable components and instructions, and processor 714 to facilitate operation of the computer executable components and instructions by external monitoring device 116. The external monitoring device 116 also includes a bus 708 that couples the various components of the external monitoring device 116, including the communication component 702, the monitoring component 704, the authorization component 706, the transmitter/receiver 710, the memory 712, and the processor 714. Repetitive description of like elements employed in other embodiments described herein is omitted for sake of brevity.

With reference to FIGS. 1, 2, and 7, the communication component 602 can be configured to facilitate telemetry communication between external monitoring device 116 and the implantable device 104. The communication component 602 can also facilitate communication between the external monitoring device 116 and other devices (e.g., external clinician device 120, a server device, or another suitable device). Communication component 702 can perform one or more of the same or similar functions as communication component 602 in some embodiments. For example, communication component 702 can control operation of the transmitter/receiver 710 to establish a monitoring telemetry session with the implantable device and control transmission and reception of data packets by the external monitoring device 116.

Communication component 702 can facilitate telemetry communication between the external monitoring device 116 and the implantable device 104 using a variety of networks (not shown) and/or wireless communication protocols. For example, in one or more embodiments, communication component 702 can communicate with implantable device 104 or another device (e.g., external clinician device 120, or another device) using NFC, or another type of communication protocol over a PAN or a LAN, (e.g., a Wi-Fi network) that can provide for communication over greater distances than NFC protocol or that can provide various advantages (such as increased security).

In some embodiments, communication component 702 can control transmission and reception of data packets via a communication channel associated with a communication protocol utilizing lower energy consumption than a conventional communication protocol for wirelessly transmitting data. For example, in a non-limiting example, communication component 702 controls transmission and reception of data packets using BLE protocol. Other communication protocols that can be employed by communication component 702 to communicate with implantable device 104 can include, but are not limited to, other BLUETOOTH® communication protocols, a Session Initiation Protocol (SIP) based protocol, a Zigbee® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, a radio frequency (RF) communication protocol, and/or other proprietary and non-proprietary communication protocols.

In some embodiments, communication component 702 can control transmission and reception of data packets via a communication channel associated with a communication protocol utilizing lower energy consumption than a conventional communication protocol for wirelessly transmitting data. In a non-limiting example, the communication component 702 controls transmission and reception of data packets using BLE protocol. Other communication protocols that can be employed by the communication component 702 to communicate with external monitoring device 116 and/or external clinician device 120 can include, but are not limited to, other BLUETOOTH® communication protocols, a Session Initiation Protocol (SIP) based protocol, a Zigbee® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, a radio frequency (RF) communication protocol, and/or other proprietary and non-proprietary communication protocols.

In various embodiments, communication component 702 can be configured to facilitate telemetry communication between the external clinician device 120 and the implantable device 104 in association with a monitoring session. For example, after a monitoring session is established between the implantable device and the external monitoring device 116, the communication component 702 can receive information monitored by the implantable device and transmitted to the external monitoring device 116 (e.g., physiological information captured from the patient by the implantable device 104, operating information monitored by the implantable device 104, etc.).

In one or more embodiments, communication component 702 can be configured to establish a secure or trusted telemetry session with implantable device 104 prior to facilitating the exchange of sensitive data between with the implantable device 104. The authorization component 706 can facilitate establishing a secure and trusted connection with the implantable device. For example, in order to establish a monitoring session with the implantable device, the authorization component 706 can include authorization information in a monitoring session request sent by the external monitoring device to the implantable device104. In some embodiments, the authorization information includes information for the external monitoring device 116 that uniquely identifies the external monitoring device 116 (e.g., a device identification number, an encrypted key, a MAC, or other suitable authentication information). This authentication information can be previously provided to the implantable device 104 and stored in the memory 620 of the implantable device as authorized device information 622. The implantable device 104 can process the received authorization information to determine whether the external monitoring device 116 is authorized to communicate with the implantable device 104. In some implementations, the external monitoring device 116 is paired with the implantable device 104.

The monitoring component 704 can be configured to facilitate establishing and performing a monitoring session with the implantable device 104. For example, the monitoring component 704 can determine when to respond to an advertisement data packet received from the implantable device 104 while the implantable device is operating in the first advertising mode. For instance, the implantable device 104 can be configured to respond according to a defined schedule (e.g., once a day, twice a day, every hour, etc.) or in response to a trigger event. The monitoring component 704 can further direct the communication component 702 to send a monitoring session request accordingly. The monitoring component 704 can request specific information from the implantable device or receive defined information from the implantable device during the monitoring session. The monitoring component 704 can further determine if a monitoring session is complete and close the monitoring session.

Figure 8:
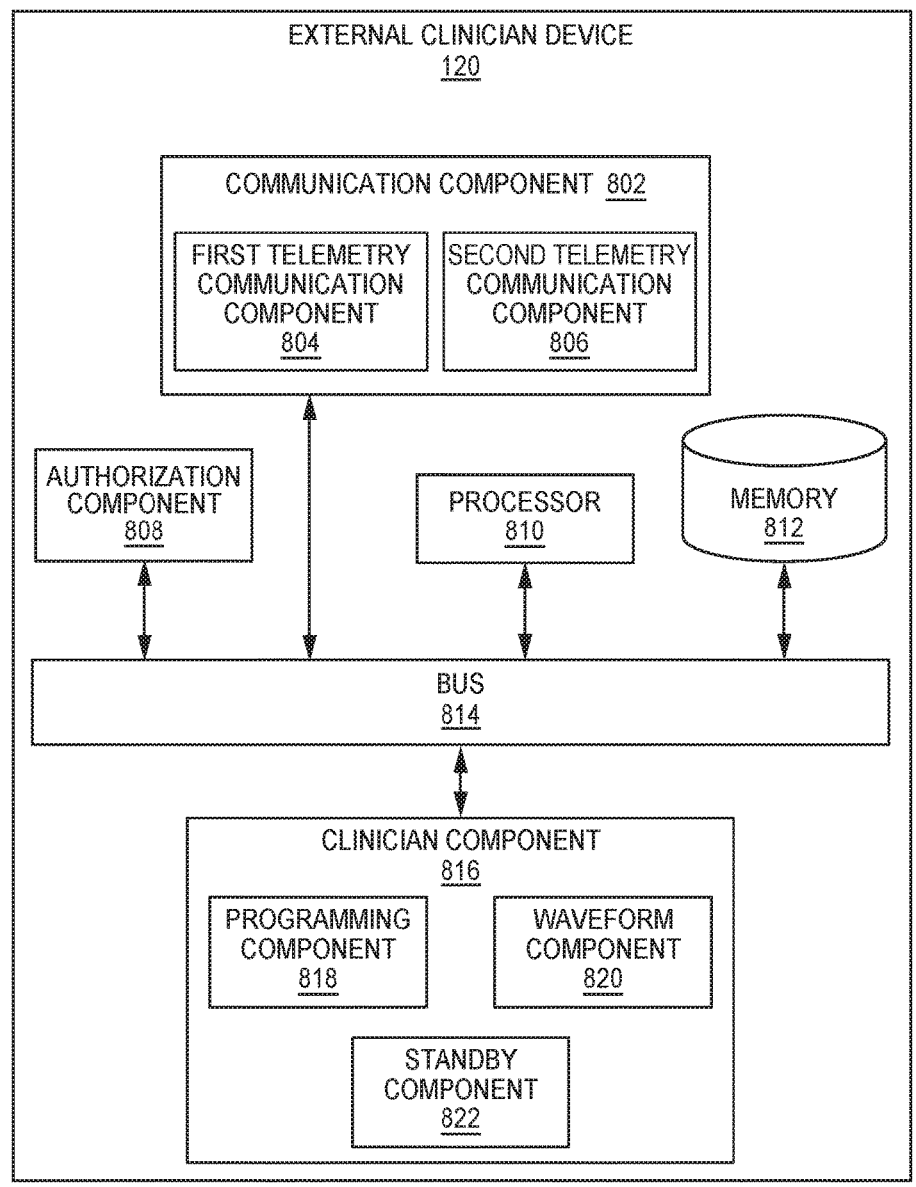
FIG. 8 illustrates a block diagram of an example, non-limiting external clinician device in accordance with one or more embodiments described herein.

FIG. 8 illustrates a block diagram of an example, non-limiting external clinician device (e.g., external clinician device 120) in accordance with one or more embodiments described herein. The external clinician device 120 can include any suitable computing device that can be operated by a clinician and configured to communicate with the implantable device 104 using a first (e.g., RF) telemetry communication protocol/technology and a second (e.g., induction) telemetry communication protocol/technology. For example, the external clinician device 120 can include a smartphone, a tablet, a dedicated handheld device, a wearable device, or another suitable device. In some embodiments, the external clinician device 120 can include an output and/or input device such as a display, a speaker, a microphone, a keypad, a touchscreen etc. In other embodiments, the external clinician device 120 can be configured to communicate with another external device to receive input and/or render output.

The external clinician device 120 includes communication component 802, authorization component 808 and clinician component 816. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

External clinician device 120 can include memory 812 configured to store computer executable components and instructions. External clinician device 120 can also include a processor 810 to facilitate operation of the instructions (e.g., computer executable components and instructions) by the external clinician device 120. External clinician device 120 can include a bus 814 that couples the various components of the external clinician device 120, including but not limited to, the communication component 802, the authorization component 808, the clinician component 816, the processor 810, and the memory 812. Repetitive description of like elements employed in other embodiments described herein is omitted for sake of brevity.

With reference to FIGS. 1, 2, and 8, the communication component 802 can be configured to facilitate telemetry communication between the external clinician device 120 and the implantable device 104. The communication component 802 can also facilitate communication between the external clinician device 120 and one or more other external devices (e.g., external monitoring device 116, a server device, or another device). The communication component 802 can provide one or more of the same or similar features and/or functionalities as communication component 602. For example, communication component 802 can include a first telemetry communication component 804 that provides same or similar features and functionality as first telemetry communication component 604. Communication component 802 can also include second telemetry communication component 806 that provides same or similar features and functionalities as second telemetry communication component 606.

In one or more embodiments, communication component 802 can be configured to establish a secure or trusted telemetry session with the implantable device 104 prior to facilitating the exchange of sensitive data between the implantable device 104 and the external clinician device 120. The authorization component 808 can facilitate establishing a trusted clinician session between the external clinician device 120 and the implantable device. For example, the authorization component 808 can direct the second telemetry communication component 806 to generate and send an external clinician initiation request to the implantable device 104 using an induction signal and include a unique identifier for the external clinician device in the clinician session initiation request (e.g., an RFM address). The second telemetry communication component 806 can further receive a response signal to the clinician session initiation request from the implantable device 104 via an induction signal and the authorization component 808 can extract authorization information included in the response signal. In one or more implementations, the authorization information includes a unique session identifier and one or more session keys. The authorization component 808 can further store the authorization information in memory 812. The authorization component 808 can further identify advertisement data packets transmitted by the implantable device based on inclusion and recognition of the session identifier in the advertisement data packets. The authorization component 808 can then direct the first telemetry communication component 804 to send a connection request to the implantable device and include the unique identifier for the external clinician device in the connection request. The implantable device 104 can then establish an authorized clinician session with the external clinician device 120. After the clinician session is established, the first telemetry communication component 804 can employ the one or more session keys to encrypt and decrypt information communicated between the implantable device 104 and the external clinician device 120.

The external clinician device 120 includes clinician component 816 to facilitate establishing and conducting a clinician session with the implantable device 104. For example, the clinician component 816 can facilitate requesting specific information from the implantable device and sending specific information to the implantable device 104. The clinician component 816 can include programming component 818, waveform component 820 and standby component 822. The programming component 818 can facilitate generating and sending programming commands to the implantable device 104. The waveform component 820 can facilitate activating and deactivating a waveform mode of the implantable device 104 and receiving live waveform data from the implantable device 104. The standby component 822 can facilitate requesting entry of and exit of the implantable device 104 to and from the standby mode. For example, in one or more embodiments, the external clinician device 120 is configured to manage entry and exit of the implantable device to and from the standby mode 205. For example, while operating in the clinician session mode 206, the external clinician device 120 can send the implantable device a command to enter standby mode. The implantable device can further be configured to enter standby mode only in response to reception of this command from the external clinician device during an established clinician session with the external clinician device. Likewise, while operating in the standby mode 205, the external clinician device 120 can send the implantable device a command to exit standby mode. The implantable device can further be configured to exit standby mode only in response to reception of this exit standby mode command.

Figure 9:
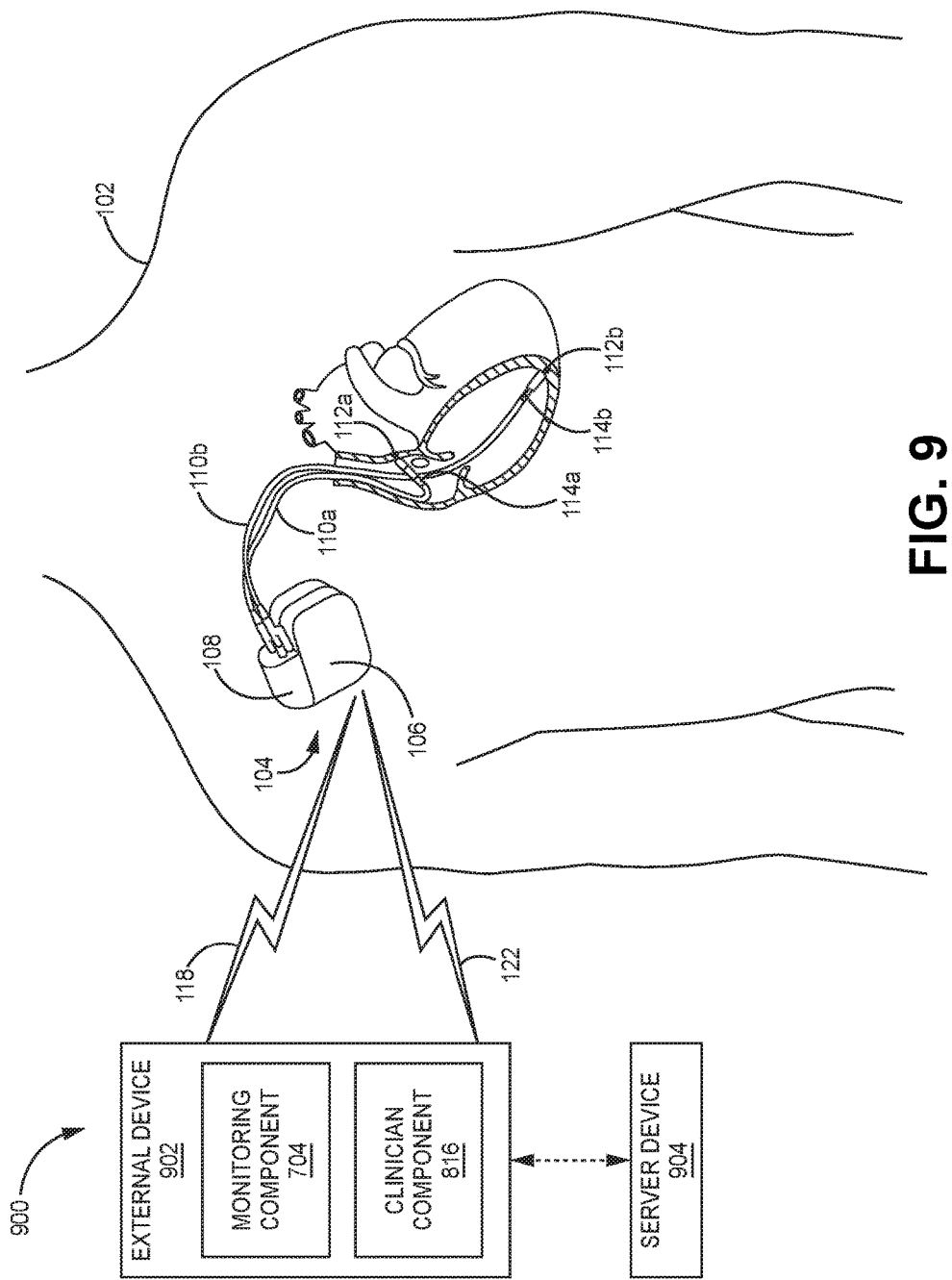
FIG. 9 illustrates a schematic diagram of another example, non-limiting medical device telemetry system configured to facilitate managing telemetry communication modes of an implantable device in accordance with one or more embodiments described herein.

FIG. 9 illustrates a schematic diagram of another example, non-limiting medical device telemetry system 900 configured to facilitate managing telemetry communication modes of operation of an implantable device in accordance with one or more embodiments described herein. System 900 includes same or similar features as medical device telemetry system 100. Unlike medical device telemetry system 100, system 900 does not include an external monitoring device 116 and an external clinician device 120. Rather, one or more the features and functionalities of external monitoring device 116 and external clinician device 120 are provided on a single external device. For example, the external device 902 can include an monitoring component 704 and an clinician component 816. In various embodiments, the external device 902 can operate in the capacity of an external monitoring device (e.g., external monitoring device 116) via usage of the monitoring component 704 and in the capacity of an external clinician device (e.g., clinician component 816) via usage of the clinician component 816.

System 900 also includes a server device 904. In various embodiments, the external device 902 can communicate with the server device using one or more of the wired or wireless communication technologies and protocols described herein. In one or more embodiments, the external device 902 can be configured to send the server device 904 information received by the external device 902 from the implantable device 104 (e.g., monitored physiological information, operational information associated with the implantable device, real-time waveform data received from the implantable device, etc.). The server device 904 can also send the external device 902 information associated with performing telemetry communication with the implantable device 104. For example, the server device 904 can send the external device 902 authorization information needed to establish an authorized monitoring session with the implantable device 104. In another example, the server device 904 can send the external device 902 programming information for providing, by the external device 902 via the clinician component 816, to the implantable device 104. Repetitive description of like elements employed in respective embodiments is omitted for sake of brevity.

Figure 10:
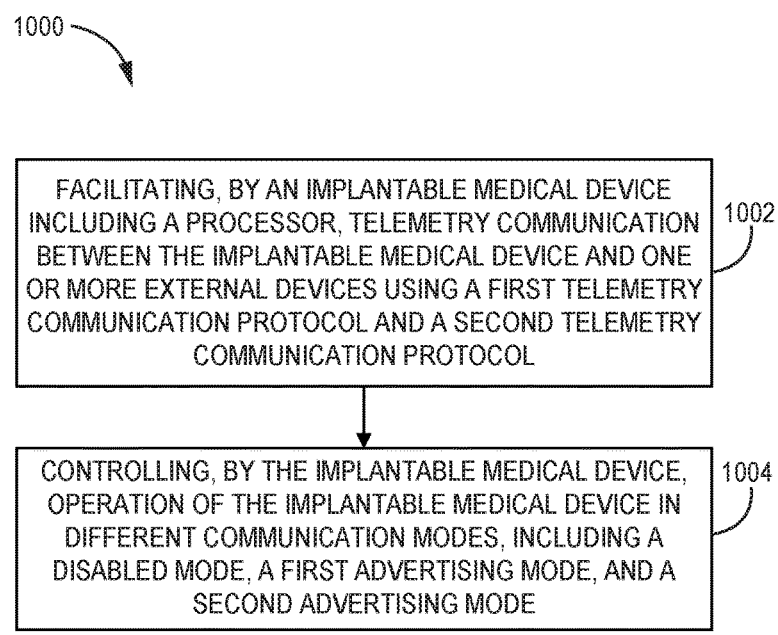
FIGS. 10-12 illustrate flow diagrams of example, non-limiting methods that facilitate managing telemetry communication modes of an implantable device in accordance with one or more embodiments described herein.
Figure 11:
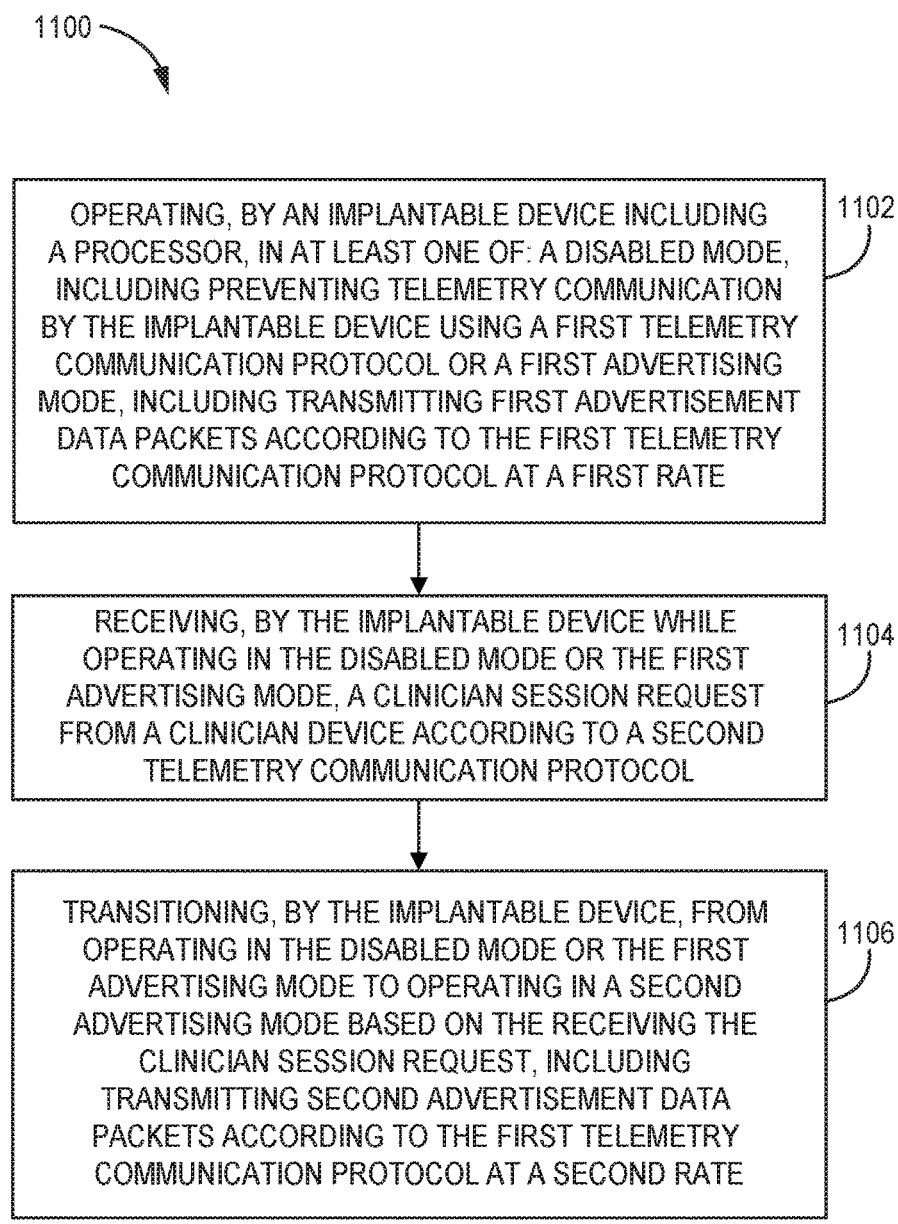
Figure 12:
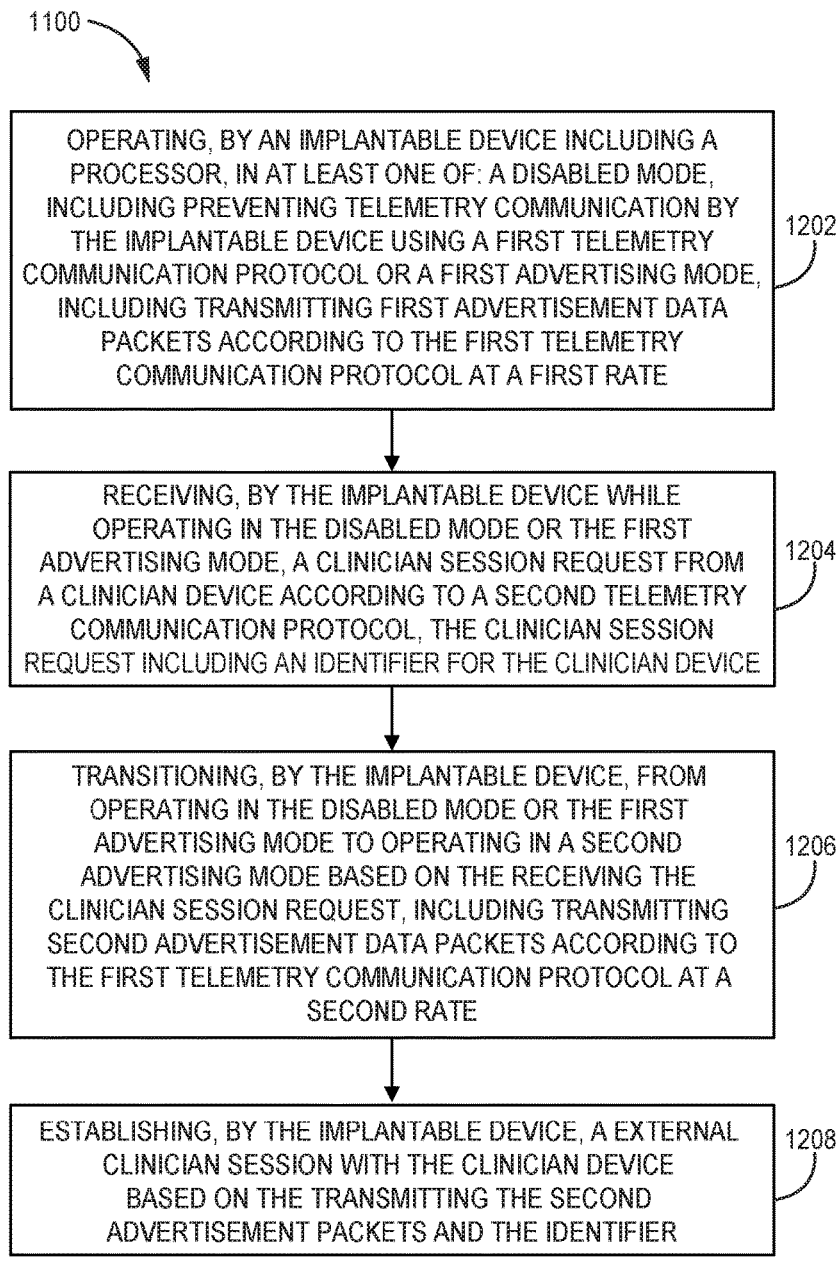

FIGS. 10-12 illustrate flow diagrams of example, non-limiting methods that facilitate managing operation of an implantable device (e.g., implantable device 104) in different communication modes of operation in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

The subject methods facilitate enhanced battery conservation associated with telemetry operations of an implantable device (e.g., implantable device 104) by employing different communication modes of operation that are respectively associated with different amounts of battery drain The different amounts of battery draw associated with these different communication modes are attributed to activation of different types of telemetry hardware circuitry components of the implantable device (e.g., RF components and induction components), and different amounts of activation of the respective telemetry hardware circuitry components (e.g., different duty cycles for receiver and transmitter activation). Because activation and deactivation of different telemetry hardware circuitry components involve physical and electrical processes and components, a human is unable to replicate or perform the subject battery conservation techniques. In addition, the subject battery conservation techniques provide substantial improvements in the field of implantable device telemetry operations while facilitating different types of telemetry communication by an implantable device. System 100 further provides substantial improvements in the field of implantable medical device telemetry security. In particular, the following methods facilitate enhanced security associated with establishing and performing a telemetry session with the implantable device (e.g., implantable device 104) using an RF-based telemetry communication technology/protocol (e.g., BLE) that enables rapid (and high power consuming) bi-directional telemetry communication with the implantable device 104 of data considered highly invasive or sensitive (e.g., programming data or waveform data associated with a clinician session).

Referring now to FIG. 10, shown is a flow diagram of an example method 1000 configured to facilitate managing telemetry communication modes of operation of an implantable device in accordance with one embodiment. In some embodiments of method 1000, an implantable device (e.g., implantable device 104) employs a communication component (e.g., communication component 602), an authorization component (e.g., authorization component 610) and a communication mode management component (e.g., communication mode management component 608) to manage operation of the implantable device using a plurality of different communication modes of operation. Repetitive description of like elements employed in other embodiments described herein is omitted for sake of brevity.

At 1002, the implantable medical device (e.g., implantable device 104) can facilitate managing telemetry communication between the implantable device and one or more external devices using a first telemetry communication protocol (e.g., BLE) and a second telemetry communication protocol (e.g., induction). At 1004, the implantable medical device can control operation of the implantable medical device in different communication modes of operation, including a disabled mode (e.g., disabled mode 201), a first advertising mode (e.g., first advertising mode 203) and a second advertising mode (e.g., second advertising mode 204). For example, during the disabled mode, the implantable device (e.g., via communication mode management component 608) can prevent telemetry communication between the implantable device and the one or more external devices according to the first telemetry communication protocol and enable telemetry communication between the implantable device and the one or more external devices according to the second telemetry communication protocol. During the first advertising mode, the implantable device can facilitate establishment of a first type of telemetry communication session (e.g., a monitoring session) between the implantable device and the one or more external devices (e.g., external monitoring device 116 or external device 902) using the first telemetry communication protocol. During the second advertising mode, the implantable device can facilitate establishment of a second type of telemetry communication session (e.g., a clinician session) between the implantable device and the one or more external devices (e.g., external clinician device 120 or external device 902) using the first telemetry communication protocol. In an embodiment, during the first advertising mode, the implantable device can transmit (e.g., via first telemetry communication component 604) one or more first advertisement data packets according to the first telemetry communication protocol at a first defined rate (e.g., once every three minutes), and during the second advertising mode the implantable device can transmit (e.g., via first telemetry communication component 604) one or more second advertisement data packets according to the first telemetry communication protocol at a second defined rate (e.g., once every second). The second defined rate can be faster than the first defined rate in some embodiments.

Turning now to FIG. 11, shown is a flow diagram of an example method 1100 configured to facilitate managing telemetry communication modes of operation of an implantable device in accordance with one embodiment. In some embodiments of method 1100, an implantable device (e.g., implantable device 104) employs a communication component (e.g., communication component 602), an authorization component (e.g., authorization component 610) and/or a communication mode management component (e.g., communication mode management component 608) to manage operation of the implantable device using a plurality of different communication modes of operation. Repetitive description of like elements employed in other embodiments described herein is omitted for sake of brevity.

At 1102, an implantable device including a processor can operate in a disabled mode (e.g., disabled mode 201) or a first advertising mode (e.g., first advertising mode 203). While operating in the disabled mode, the implantable device can prevent telemetry communication by the implantable device using a first telemetry communication protocol. While operating in the first advertising mode, the implantable device can transmit first advertisement data packets according to the first telemetry communication protocol at a first rate (e.g., once every three minutes). At 1104, while operating in the disabled mode or the first advertising mode, the implantable device can receive a clinician session request from a clinician device according to a second telemetry communication protocol (e.g., via an induction signal). At 1106, the implantable device can transition from operating in the disabled mode or the first advertising mode to operating in a second advertising mode based on receiving the clinician session request. While operating in the second advertising mode, the implantable device can transmit second advertisement data packets according to the first telemetry communication protocol at a second rate. In one or more implementations, the second rate is faster than the first rate.

Referring now to FIG. 12, shown is a flow diagram of another example method 1200 configured to facilitate managing telemetry communication modes of operation of an implantable device in accordance with one or more embodiments. In some embodiments of method 1200, an implantable device (e.g., implantable device 104) employs a communication component (e.g., communication component 602), an authorization component (e.g., authorization component 610) and a communication mode management component (e.g., communication mode management component 608) to manage operation of the implantable device using a plurality of different communication modes of operation. Repetitive description of like elements employed in other embodiments described herein is omitted for sake of brevity.

At 1202, an implantable device including a processor (e.g., implantable device 104) can operate in a disabled mode (e.g., disabled mode 201) or a first advertising mode (e.g., first advertising mode 203). While operating in the disabled mode, the implantable device can prevent telemetry communication by the implantable device using a first telemetry communication protocol. While operating in the first advertising mode, the implantable device can transmit first advertisement data packets according to the first telemetry communication protocol at a first rate (e.g., once every three minutes). At 1204, while operating in the disabled mode or the first advertising mode, the implantable device can receive a clinician session request from a clinician device according to a second telemetry communication protocol (e.g., via an induction signal). The clinician session request can include an identifier for the clinician device.

At 1206, the implantable device can transition from operating in the disabled mode or the first advertising mode to operating in a second advertising mode based on receiving the clinician session request. While operating in the second advertising mode, the implantable device can transmit second advertisement data packets according to the first telemetry communication protocol at a second rate. In one or more implementations, the second rate is faster than the first rate.

At 1208, the implantable device can establish a clinician session with the clinician device based on transmitting the second advertisement data packets and the identifier. For example, in response to receiving the clinician session request, the implantable device can generate (e.g., via authorization component 610) session authorization information including a unique session identifier and one or more unique session keys. The implantable device can send the session authorization information to the clinician device using the second telemetry communication protocol. The implantable device can then begin transmitting the second advertisement data packets, which included the unique session identifier. The clinician device can receive the second advertisement data packets and recognize the unique session identifier in the second advertisement data packets. Based on recognition of the unique session identifier, the clinician device can send a connection request to the implantable device including the identifier for the clinician device. The implantable device can be configured to accept only connection requests received from the clinician device that provided the clinician session request using the second telemetry communication protocol and including the identifier for the clinician device. The implantable device can determine that the connection request was provided by the clinician device based on recognition of the identifier for the clinician device.

Figure 13:
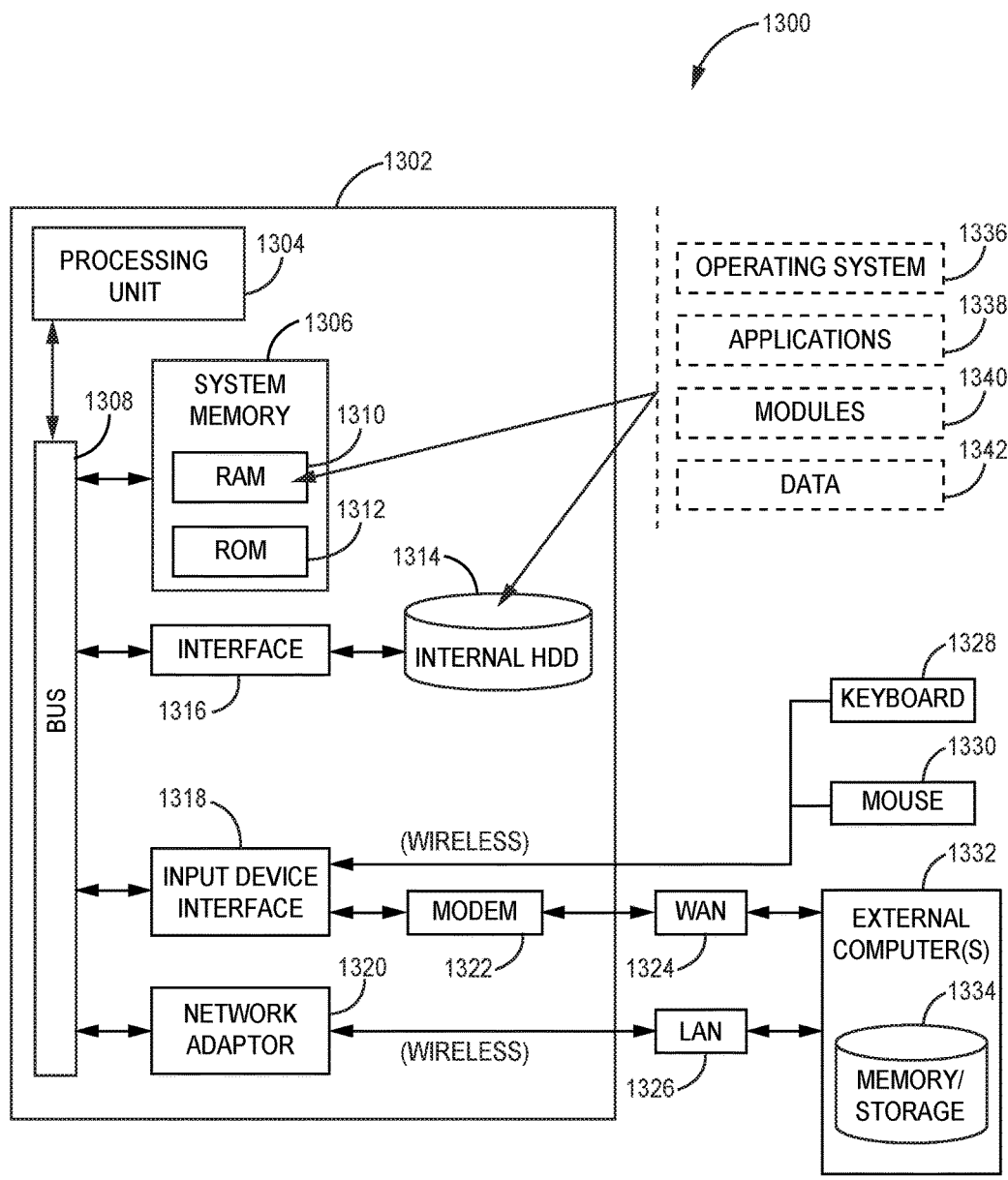
FIG. 13 illustrates a block diagram of an example, non-limiting computer operable to facilitate managing telemetry communication modes of an implantable device in accordance with one or more embodiments described herein.

FIG. 13 illustrates a block diagram of an example, non-limiting computer operable to facilitate managing telemetry communication modes of an implantable device in accordance with one or more embodiments described herein. For example, in some embodiments, the computer can be or be included within implantable device 104, external monitoring device 116, external clinician device 120, external device 902 and/or server device 904. Repetitive description of like elements employed in other embodiments described herein is omitted for sake of brevity.

In order to provide additional context for one or more embodiments described herein, FIG. 13 and the following discussion are intended to provide a brief, general description of a suitable computing environment 1300 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or external computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 13, example environment 1300 that can be employed to implement one or more embodiments of the embodiments described herein includes computer 1302. Computer 1302 includes processing unit 1304, system memory 1306 and system bus 1308. System bus 1308 couples system components including, but not limited to, system memory 1306 to processing unit 1304. Processing unit 1304 can be any of various commercially available processors. Dual microprocessors and other multiprocessor architectures can also be employed as processing unit 1304.

System bus 1308 can be any of several types of bus structure that can further interconnect to a memory bus (with or without a memory controller), a peripheral bus, and a local bus using any of a variety of commercially available bus architectures. System memory 1306 includes RAM 1310 and ROM 1312. A basic input/output system (BIOS) can be stored in a non-volatile memory such as ROM, erasable programmable read only memory (EPROM), EEPROM, which BIOS contains the basic routines that help to transfer information between elements within computer 1302, such as during startup. RAM 1310 can also include a high-speed RAM such as static RAM for caching data.

Computer 1302 further includes internal hard disk drive (HDD) 1314 (e.g., Enhanced Integrated Drive Electronics (EIDE), Serial Advanced Technology Attachment (SATA)). HDD 1314 can be connected to system bus 1308 by hard disk drive interface 1316. The drives and their associated computer-readable storage media provide nonvolatile storage of data, data structures, computer-executable instructions, and so forth. For computer 1302, the drives and storage media accommodate the storage of any data in a suitable digital format.

A number of program modules can be stored in the drives and RAM 1310, including operating system 1336, one or more application programs 1338, other program modules 1340 and program data 1342. All or portions of the operating system, applications, modules, and/or data can also be cached in RAM 1310. The systems and methods described herein can be implemented utilizing various commercially available operating systems or combinations of operating systems.

A mobile device can enter commands and information into computer 1302 through one or more wireless input devices, e.g., wireless keyboard 1328 and a pointing device, such as wireless mouse 1330. Other input devices (not shown) can include a smart phone, tablet, laptop, wand, wearable device or the like. These and other input devices are often connected to the processing unit 1304 through input device interface 1318 that can be coupled to system bus 1308, but can be connected by other interfaces, such as a parallel port, an IEEE serial port, a game port and/or a universal serial bus (USB) port.

Computer 1302 can operate in a networked environment using logical connections via wired and/or wireless communications to one or more external computers, such as external computer(s) 1332. External computer(s) 1332 can be a workstation, a server computer, a router, a personal computer, portable computer, microprocessor-based entertainment appliance, a peer device or other common network node, and typically includes many or all of the elements described relative to computer 1302, although, for purposes of brevity, only memory/storage device 1334 is illustrated. The logical connections depicted include wired/wireless connectivity to a local area network (LAN) 1326 and/or larger networks, e.g., WAN 1324, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1302 can be connected to local network through a wired and/or wireless communication network interface or adapter 1320. Adapter 1320 can facilitate wired or wireless communication to LAN 1326, which can also include a wireless access point (AP) connected to the LAN 1326 for communicating with adapter 1320.

When used in a WAN networking environment, computer 1302 can include modem 1322 or can be connected to a communications server on WAN 1324 or has other apparatus for establishing communications over WAN 1324, such as by way of the Internet. Modem 1322, which can be internal or external and a wired or wireless device, can be connected to system bus 1308 via input device interface 1318. In a networked environment, program modules depicted relative to computer 1302 or portions thereof, can be stored in an external memory/storage device. It will be appreciated that the network connections shown are example and other apparatus of establishing a communications link between the computers can be used.

Computer 1302 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 13 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, $x=(x1, x2, x3, x4, \ldots, xn)$, to a confidence that the input belongs to a class, that is, $f(x)=$confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a defined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A device comprising:
a communication component configured to facilitate telemetry communication between the device and a second device using a first telemetry communication protocol to communicate data; and
a communication mode management component configured to control operation of the device in a plurality of communication modes, the plurality of communication modes including:
a first advertising mode configured to facilitate establishment of a first type of telemetry communication session between the device and the second device using the first telemetry communication protocol; and
a second advertising mode configured to facilitate establishment of a second type of telemetry communication session between the device and the second device using the first telemetry communication protocol, wherein the device transitions from the first advertising mode to the second advertising mode in response to receiving a request for the second type of telemetry communication session.

2. The device of claim 1, wherein the first type of telemetry communication session is more restrictive than the second type of communication session.

3. The device of claim 2, wherein the first type of telemetry communication session only permits reading of stored data and the second type of communication session permits reading of stored data and programming of operating parameters of the device.

4. The device of claim 2, wherein the first type of telemetry communications session only permits reading of previously stored data and the second type of communication session permits reading of previously stored data and obtaining real-time data.

5. The device of claim 2, further comprising circuitry configured to at least one of obtain sensed physiological data associated with a patient or deliver a therapy to the patient, wherein the first type of telemetry communication session permits reading of sensed physiological data associated with the patient and the second type of communication session permits directing the medical device to provide the therapy.

6. The device of claim 1, wherein, during the first advertising mode, the communication component is further configured to transmit a plurality of first advertisement data packets according to the first telemetry communication protocol at a first defined rate, and wherein, during the second advertising mode, the communication component is further configured to transmit a plurality of second advertisement data packets according to the first telemetry communication protocol at a second defined rate, wherein the second defined rate is faster than the first defined rate.

7. The device of claim 1, wherein, during the first advertising mode, the communication component is further configured to transmit a plurality of first advertisement data packets according to the first telemetry communication protocol for a first duration of time, and wherein, during the second advertising mode, the communication component is further configured to transmit a plurality of second advertisement data packets according to the first telemetry communication protocol for a second duration of time, wherein the second duration of time is longer than the first duration of time.

8. The device of claim 1, wherein
the communication component comprises a first communication component, the device further comprising a second communication component configured to facilitate telemetry communication between the device and a second device using a second telemetry communication protocol,
the communication mode management component is further configured to transition operation of the implantable device from the first advertising mode to the second advertising mode based on reception, by the communication component, of the request via the second telemetry communication protocol to establish the second type of telemetry communication session.

9. The device of claim 8, wherein the first telemetry communication protocol comprises Bluetooth Low Energy communication protocol and the second telemetry communication protocol comprises an induction-based wireless communication protocol.

10. The device of claim 8, wherein the plurality of communication modes further includes a disabled mode configured to prevent telemetry communication between the device and the second device according to the first telemetry communication protocol and enable telemetry communication between the device and the second device according to the second telemetry communication protocol, the communication mode management component being configured to transition operation of the implantable device from the disabled mode to the second advertising mode in response to receiving a request via the second telemetry communication protocol for the second type of telemetry communication session.

11. The device of claim 1, wherein the communication mode management component is configured to transition operation of the implantable device from the second advertising mode to the first advertising mode based on failure of the device and the second device associated with the request to establish the second type of telemetry communication session within a defined time period.

12. The device of claim 1, wherein the device further comprises a housing configured for implantation within a patient, the communication component and the communication mode management component contained within the housing,
wherein the plurality of communication modes further includes a disabled mode configured to prevent telemetry communication between the device and the second device according to the first telemetry communication protocol, the communication mode management component being configured to transition from the disabled mode to the first advertising mode in response to implantation detection.

13. A method comprising:
operating a communication component of a first device in a first advertising mode configured to facilitate establishment of a first type of telemetry communication session between the first device and a second device using a first telemetry communication protocol;
receiving a request for a second type of telemetry communication session between the first device and the second device, the second type of telemetry communication session being more restrictive than the first type of telemetry communication session;
transitioning the communication component of the first device from the first advertising mode to a second advertising mode in response to receiving the request, the second advertising mode configured to facilitate establishment of the second type of telemetry communication session between the first device and the second device using the first telemetry communication protocol.

14. The method of claim 13, further comprising:
permitting the second device to only read stored data in the first type of telemetry communication session; and
permitting the second device to read stored data and program operating parameters of the first device the second type of communication session permits.

15. The method of claim 13, further comprising:
permitting the second device to only read previously stored data in the first type of telemetry communication session; and
permitting the second device to read previously stored data and obtain real-time data stored data in the second type of communication session.

16. The method of claim 13, wherein, while operating in the first advertising mode, transmitting a plurality of first advertisement data packets according to the first telemetry communication protocol at a first defined rate, and further wherein, while operating in the second advertising mode, transmitting a plurality of second advertisement data packets according to the first telemetry communication protocol at a second defined rate, wherein the second defined rate is faster than the first defined rate.

17. The method of claim 13, wherein, while operating in the first advertising mode, transmitting one or more advertisement data packets according to the first telemetry communication protocol for a first duration of time, and further wherein, while operating in the second advertising mode, transmitting one or more second advertisement data packets according to the first telemetry communication protocol for a second duration of time, wherein the second duration of time is longer than the first duration of time.

18. The method of claim 13, wherein receiving the request for the second type of telemetry communication session comprises receiving the request via a second communication component configured to facilitate telemetry communication between the first device and the second device using a second telemetry communication protocol.

19. The method of claim 13, further comprising:

determining that the first device and the second device fail to establish the second type of telemetry communication session within a defined time period; and transitioning the communication component from the second advertising mode to the first advertising mode in response to the determination.

20. The method of claim 13, further comprising:

operating the first device in a disabled mode configured to prevent telemetry communication between the first device and the second device according to the first telemetry communication protocol and enable telemetry communication between the first device and the second device according to a second telemetry communication protocol;

while operating in the disabled mode, receiving the request via the second telemetry communication protocol for the second type of telemetry communication session; and transitioning operation of the communication component of the first device from the disabled mode to the second advertising mode in response to receiving the request.

21. The method of claim 13, operating the first device in a disabled mode configured to prevent telemetry communication between the first device and the second device according to the first telemetry communication protocol and enable telemetry communication between the first device and the second device according to a second telemetry communication protocol;

while operating in the disabled mode, detecting implantation of the first device; and transitioning operation of the communication component of the first device from the disabled mode to the first advertising mode in response to detecting implantation.

\* \* \* \* \*